US007371757B2

(12) United States Patent
Morningstar et al.

(10) Patent No.: US 7,371,757 B2
(45) Date of Patent: May 13, 2008

(54) FUSED HETEROCYCLES AS INHIBITORS OF GLUTAMATE RACEMASE(MURI)

(75) Inventors: Marshall Morningstar, Waltham, MA (US); Gregory Basarab, Waltham, MA (US); Charles Joseph Eyermann, Waltham, MA (US); Madhu Gowravaram, Waltham, MA (US); Oluyinka Green, Waltham, MA (US); Andrew Kiely, Cambridge, MA (US); Lawrence MacPherson, Waltham, MA (US); Nguyen Thanh, La Jolla, CA (US)

(73) Assignee: AstraZeneca AB, Sodertalje (SE)

( * ) Notice: Subject to any disclaimer, the term of this patent is extended or adjusted under 35 U.S.C. 154(b) by 188 days.

(21) Appl. No.: 10/567,797

(22) PCT Filed: Aug. 12, 2004

(86) PCT No.: PCT/GB2004/003464

§ 371 (c)(1),
(2), (4) Date: Feb. 9, 2006

(87) PCT Pub. No.: WO2005/016929

PCT Pub. Date: Feb. 24, 2005

(65) Prior Publication Data

US 2006/0252781 A1 Nov. 9, 2006

Related U.S. Application Data

(60) Provisional application No. 60/495,615, filed on Aug. 15, 2003.

(51) Int. Cl.
*A01N 43/54* (2006.01)
*A61K 31/505* (2006.01)
*C07D 239/00* (2006.01)
*C07D 471/00* (2006.01)
*C07D 487/00* (2006.01)
*C07D 491/00* (2006.01)

(52) U.S. Cl. ...................................... 514/267; 544/251
(58) Field of Classification Search ...................... None
See application file for complete search history.

(56) References Cited

FOREIGN PATENT DOCUMENTS

WO　　WO 03/002567　　1/2003
WO　　WO 2005/016929　　2/2005

OTHER PUBLICATIONS

Abdelhamid, et al., A Facile Synthesis of Pyrimido[2",3":5',1']pyrazolo[3',4':4,5]pyrimido[1,6-a]benzimidazoles and [1,2,4]triazino[3",4":5',1']pyrazolo[3',4':4,5]-pyrimido[6,1-a]benzimidazoles, Indian Journal of Chemistry, vol. 40B, 284-89 (2001).*
Ghorab, Moustafa M, Synthesis and Radiation Stability of some new biologically active pyrazolo [3,4-d]pyrimidines, 2000, pp. 93-110, National Center for Radiation Research and Technology, Egypt.

* cited by examiner

Primary Examiner—James O. Wilson
Assistant Examiner—Erich Leeser

(57) ABSTRACT

This invention relates to novel compounds having formula: (I) or (II) and to their pharmaceutical compositions and to their methods of use. These novel compounds provide a treatment or prophylaxis of *H. pylori* infection.

17 Claims, No Drawings

FUSED HETEROCYCLES AS INHIBITORS OF GLUTAMATE RACEMASE(MURI)

CROSS-REFERENCE TO RELATED APPLICATIONS

This application is a US National Stage under 35 U.S.C § 371 of International Application No. PCT/GB2004/003464 (filed Aug. 12, 2004) which claims priority under 35 U.S.C. § 111 to Application No. 60/495,615 filed on Aug. 15, 2003, the specification of which is incorporated by reference herein.

FIELD OF THE INVENTION

The present invention relates to novel fused heterocycles, their pharmaceutical compositions and methods of use. In addition, the present invention relates to therapeutic methods for the treatment and prevention of various diseases caused by Helicobacter pylori (H. pylori) infection.

BACKGROUND OF THE INVENTION

Helicobacter pylori (H. pylori) is a highly motile, S-shaped, microaerophilic gram-negative bacterium that colonizes in the stomach. H. pylori infection is widespread with seroprevalence in the developed world between 30-60%. Infection with the bacterium is usually contracted during childhood and patients remain infected for life unless treated. H. pylori infection has been shown to result in the development of gastritis, peptic ulcer, and mucosa-associated lymphoid tissue (MALT) lymphoma and has been linked to gastric adenocarcinoma (Go, M. F. and D. T. Smoot, Helicobacter pylori, gastric MALT lymphoma, and adenocarcinoma of the stomach Seminars in Gastrointestinal Disease, 2000, 11(3): p. 134-141). Eradication of H. pylori infection is currently achieved using combination therapy of antimicrobial and antisecretory agents (Malfertheiner, P., A. Leodolter, and U. Peitz, Cure of Helicobacter pylori-associated ulcer disease through eradication Bailliere's Best Practice and Research in Clinical Gastroenterology, 2000, 14(1): p. 119-132). However, compliance to these therapies is compromised due to adverse side effects and cumbersome dosing regimens. In addition, increasing prevalence of H. pylori strains resistant to existing antimicrobial therapies threatens to limit the use of these treatments (Qureshi, W. A. and D. Y. Graham, Antibiotic-resistant H. pylori infection and its treatment. Current Pharmaceutical Design, 2000, 6(15): p. 1537-1544). Given these considerations, a therapy for H. pylori infection would be a novel antimicrobial monotherapy that is selective for H. pylori eradication. The selectivity attribute is expected to aid in minimizing side effects on gut flora.

H. pylori, like all Gram positive and Gram negative bacteria, utilize a cell wall comprised of crosslinked peptidoglycan units to maintain shape and resist high osmotic pressure potentials. Bacterial cell wall biosynthesis is a validated target for antimicrobial activity; cephalosphorins, penicillins and glycopeptides are antimicrobial agents, which block cell wall biosynthesis (Walsh, C., Molecular mechanisms that confer antibacterial resistance. Nature, 2000, 406: p. 775-781). Cell wall biosynthesis requires the enzyme MurI, a glutamate racemase, and therefore this enzyme is essential for bacterial viability (Doublet, P., et al., The murI gene of Escherichia coli is an essential gene that encodes a glutamate racemase activity. Journal of Bacteriology, 1993, 175(10): p. 2970-9).

The present invention describes compounds, which specifically inhibit H. pylori MurI, compositions of such compounds and methods of use. The compounds disclosed herein represent a valuable contribution to the development of selective therapies directed to diseases resulting from H. pylori infection.

SUMMARY OF THE INVENTION

A compound having the structural formula (I):

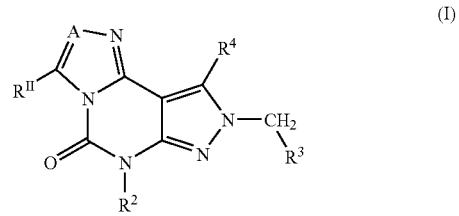

wherein,

A is N or $CR^I$;

$R^I$ is, independently at each instance, H, halogen, cyano, nitro, optionally substituted alkyl, optionally substituted alkenyl, optionally substituted alkynyl, optionally substituted alkoxy, optionally substituted amino, optionally substituted carboxy, optionally substituted carbonyl, optionally substituted carbamide, optionally substituted sulfide, optionally substituted sulphone, optionally substituted sulfoxide, optionally substituted sulphamide;

$R^{II}$ is, independently at each instance, H, halogen, cyano, nitro, optionally substituted alkyl, optionally substituted alkenyl, optionally substituted alkynyl, optionally substituted alkoxy, optionally substituted amino, optionally substituted carboxy, optionally substituted carbonyl, optionally substituted carbamide, optionally substituted sulfide, optionally substituted sulphone, optionally substituted sulfoxide, optionally substituted sulphamide;

$R^2$ is H, optionally substituted alkyl, optionally substituted alkylcycloalkyl, optionally substituted alkenyl, optionally substituted alkynyl, optionally substituted cycloalkyl, optionally substituted cycloalkenyl, optionally substituted cycloalkynyl, optionally substituted aryl, optionally substituted alkoxy, optionally substituted amino, or optionally substituted heterocycle;

$R^3$ is a monocyclic or bicyclic, saturated or unsaturated, ring system comprising 0, 1, 2 or 3 heteroatoms independently selected from N, O, or S, the ring being substituted by 0, 1, 2 or 3 substituents selected from =O, halogen, —$OR^a$, $C_{1-6}$alkyl, $C_{1-6}$haloalkyl, —CN, nitro, —$S(=O)_nR^c$, —$O(CH_2)_m$Het, —$O(CH_2)_mC(=O)$Het, —$O(CH_2)_mC(=O)NR^aR^a$, —$O(CH_2)_mC(=O)OR^a$, —$O(CH_2)_mNR^aR^a$, —$O(CH_2)_mOR^a$, —$S(CH_2)_m$Het, —$S(CH_2)_mC(=O)$Het, —$S(CH_2)_mC(=O)NR^aR^a$, —$S(CH_2)_mC(=O)OR^a$, —$S(CH_2)_mNR^aR^a$, —$S(CH_2)_mOR^a$, —$NR^aR^a$, —$NHC(=O)R^a$, $N=NR^a$, aminocarbonyl, phenyl, benzyl; or $R^3$ is represented by -Het, -Het-Het, $R^5$, —$R^5$-Het, -Het-$R^5$, -Het-O—$R^5$, —$R^5$—$R^5$—$R^5$—$OR^5$;

$R^4$ is a monocyclic or bicyclic, saturated or unsaturated, ring system, or a vicinal-fused derivative thereof, which may contain from 5 to 12, preferably 5 to 10, ring atoms, 0, 1, 2, 3 or 4 of which are heteroatoms independently selected from N, O, or S, the ring system being substituted by 0, 1, 2 or 3 substituents selected from $B(OH)_2$, vicinal —$OCH_2CH_2O$—, vicinal —$OC_{1-2}$haloalkylO—, vicinal —OCH₂O—, vicinal —CH₂OCH₂O—, =O, halogen, —R^bOR^a, —SR^a, —OR^a, C₁₋₆alkyl, C₁₋₆haloalkyl, —CN, —S(=O)ₙR^c, —O(CH₂)ₘHet, —O(CH₂)ₘC(=O)Het, —O(CH₂)ₘC(=O)NR^aR^a, —O(CH₂)ₘC(=O)OR^a, —O(CH₂)ₘNR^aR^a, —O(CH₂)ₘOR^a, —S(CH₂)ₘHet, —S(CH₂)ₘC(=O)Het, —S(CH₂)ₘC(=O)NR^aR^a, —S(CH₂)ₘC(=O)OR^a, —S(CH₂)ₘNR^aR^a, —S(CH₂)ₘOR^a, —NR^aR^a, —NHC(=O)R^a, —NHC(=O)OR^a, N=NR^a, NO₂, —C(=O)NR^aR^a, —C(=O)NR^aOR^a, —C(=O)NR^a(R^bNR^aR^a), —C(=O)NR^a(R^bOR^a), —C(=O)NR^a(R^bS(=O)ₙR^a), —C(=O)NR^a(R^bHet), —C(=O)OR^a, —OC(=O)R^a, —C(=O)OR^bNR^aR^a, —C(=O)R^a, —C(=O)R^bNR^aR^a, —C(=NOR^a)R^a, —C(=NCN)R^a, —S(=O)₂NR^aR^a, —NR^aS(=O)₂R^a, —S(=O)₂NR^a(R^bC(=O)NR^aR^a), —S(=O)₂NR^a(R^bC(=O)OR^a), aminocarbonyl, phenyl, benzyl; or R⁴ is represented by —(CH₂)ₙR⁵-Het, —(CH₂)ₙR^d, -Het, -Het-Het, R⁵, —R⁵-Het, -Het-R⁵, -Het-OR⁵, R⁵—R⁵, or —R⁵—OR⁵; or R⁴ is represented by C₁₋₆alkyl, —NC₁₋₆alkyl, or —N(C₁₋₆alkyl)₂ wherein the C₁₋₆alkyl, —NC₁₋₆alkyl, —N(C₁₋₆alkyl) are substituted by 0, 1 or 2 substituents selected from R^a, OR^a, halogen or phenyl wherein R⁴ is not —(CH₂)_zCH₃, —(CH₂)_zCH₂OH, —(CH₂)_zCO₂H, or —(CH₂)_zCO₂C₁₋₆alkyl wherein z is 1,2,3,4,5, or 6;

R⁵ is independently at each instance, phenyl substituted by 0, 1, 2, or 3 groups selected from halogen, C₁₋₆haloalkyl, —OC₁₋₆haloalkyl, C₁₋₆allyl, —CN, nitro, —OR^a, —S(=O)ₙ R^c, —O(CH₂)ₘHet, —O(CH₂)ₘC(=O)Het, —O(CH₂)ₘC(=O)NR^aR^a, —O(CH₂)ₘC(=O)OR^a, —O(CH₂)ₘNR^aR^a, —O(CH₂)ₘOR^a, —S(CH₂)ₘHet, —S(CH₂)ₘC(=O)Het, —S(CH₂)ₘC(=O)NR^aR^a, —S(CH₂)ₘC(=O)OR^a, —S(CH₂)ₘNR^aR^a, —S(CH₂)ₘOR^a, —R^bOR^a, —SR^a, —C(=O)NR^aR^a, —C(=O)NR^aOR^a, —C(=O)NR^aR^bNR^aR^a, —C(=O)NR^aR^bOR^a, —C(=O)NR^aR^bS(=O)ₙR^a, —C(=O)NR^aR^bHet, —C(=O)OR^a, —OC(=O)R^a, —C(=O)OR^bNR^aR^a, —C(=O)R^a, —C(=O)R^bNR^aR^a, —C(=NOR^a)R^a, —C(=NCN)R^a, —S(=O)₂NR^aR^a, —NR^aS(=O)₂R^a, —S(=O)₂NR^aR^bC(=O)NR^aR^a, or —S(=O)₂NR^aR^bC(=O)OR^a;

R^a is, independently at each instance, H, C₁₋₆alkyl, —C(=O)C₁₋₄alkyl, C₁₋₄haloalkyl, phenyl, benzyl, or 5 or 6-memebered ring, saturated or unsaturated heterocycle containing 1,2,3, or 4 heteroatoms independently selected from N, O or S;

R^b is, independently at each instance, C₁₋₆alkyl, —C(=O)C₁₋₄alkyl, C₁₋₄haloalkyl, phenyl, benzyl, or 5 or 6-memebered ring, saturated or unsaturated heterocycle containing 1,2,3, or 4 heteroatoms independently selected from N, O or S;

R^c is C₁₋₆alkyl, C₁₋₄haloalkyl, phenyl or benzyl;

R^d is phenyl substituted by 0, 1 or 2 groups selected from —CN, halogen, nitro, C₁₋₆alkyl, C₁₋₄haloalkyl, —OH, —OR^c, —NR^aR^a, —S(=O)ₙR^c, —C(=O)NR^aR^a, —C(=O)OR^a, —NR^aC(=O)R^a, —OC(=O)R^a, B(OH)₂, vicinyl —OCH₂CH₂O—, vicinyl —OC₁₋₂haloalkylO—, vicinyl —OCH₂O—, vicinyl —CH₂OCH₂O—, phenyl, benzyl and a 5- or 6-membered ring, saturated or unsaturated heterocycle containing 1, 2, 3 or 4 heteroatoms independently selected from N, O, or S;

m is 1, 2 or 3;

n is 0, 1 or 2;

or a pharmaceutically acceptable salt thereof.

The invention also encompasses stereoisomers, enantiomers, in vivo-hydrolysable precursors and pharmaceutically-acceptable salts of compounds of formula I, pharmaceutical compositions and formulations containing them, methods of using them to treat diseases and conditions either alone or in combination with other therapeutically-active compounds or substances, processes and intermediates used to prepare them, uses of them as medicaments, uses of them in the manufacture of medicaments and uses of them for diagnostic and analytic purposes.

DETAILED DESCRIPTION OF THE INVENTION

In a first embodiment, the present invention provides novel compounds having structural formula (I):

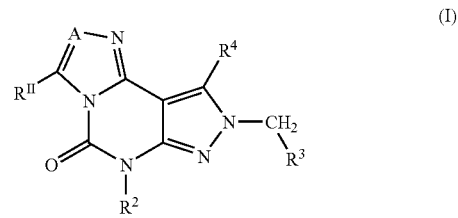

wherein,

A is N or CR^I;

R^I is, independently at each instance, H, halogen, cyano, nitro, optionally substituted alkyl, optionally substituted alkenyl, optionally substituted alkynyl, optionally substituted alkoxy, optionally substituted amino, optionally substituted carboxy, optionally substituted carbonyl, optionally substituted carbamide, optionally substituted sulfide, optionally substituted sulphone, optionally substituted sulfoxide, optionally substituted sulphamide;

R^II is, independently at each instance, H, halogen, cyano, nitro, optionally substituted alkyl, optionally substituted alkenyl, optionally substituted alkynyl, optionally substituted alkoxy, optionally substituted amino, optionally substituted carboxy, optionally substituted carbonyl, optionally substituted carbamide, optionally substituted sulfide, optionally substituted sulphone, optionally substituted sulfoxide, optionally substituted sulphamide;

R² is H, optionally substituted alkyl, optionally substituted alkylcycloalkyl, optionally substituted alkenyl, optionally substituted alkynyl, optionally substituted cycloalkyl, optionally substituted cycloalkenyl, optionally substituted cycloalkynyl, optionally substituted aryl, optionally substituted alkoxy, optionally substituted amino, or optionally substituted heterocycle;

R³ is a monocyclic or bicyclic, saturated or unsaturated, ring system comprising 0, 1, 2 or 3 heteroatoms independently selected from N, O, or S, the ring being substituted by 0, 1, 2 or 3 substituents selected from =O, halogen, —OR^a, C₁₋₆alkyl, C₁₋₆haloalkyl, —CN, nitro, —S(=O)ₙR^c, —O(CH₂)ₘHet —O(CH₂)ₘC(=O)Het, —O(CH₂)ₘC(=O)NR^aR^b, —O(CH₂)ₘC(=O)OR^a, —O(CH₂)ₘNR^aR^a, —O(CH₂)ₘOR^a, —S(CH₂)ₘHet, —S(CH₂)ₘC(=O)Het, —S(CH₂)ₘC(=O)NR^aR^a, —S(CH₂)ₘC(=O)OR^a, —S(CH₂)ₘNR^aR^a, —S(CH₂)ₘOR^a, —NR^aR^a, —NHC(=O)R^a, N=NR^a, aminocarbonyl, phenyl, benzyl; or R³ is represented by -Het, -Het-Het, R⁵, —R⁵-Het, -Het-R⁵, -Het-O—R⁵, —R⁵—R, —R⁵—OR⁵;

R⁴ is a monocyclic or bicyclic, saturated or unsaturated, ring system, or a vicinal-fused derivative thereof, which may contain from 5 to 12, preferably 5 to 10, ring atoms, 0, 1, 2, 3 or 4 of which are heteroatoms independently selected from N, O, or S, the ring system being substituted by 0, 1, 2 or 3 substituents selected from B(OH)₂, vicinal —OCH$_2$CH$_2$O—, vicinal —OC$_{1-2}$haloalkylO—, vicinal —OCH$_2$O—, vicinal —CH$_2$OCH$_2$O—, =O, halogen, —R$^b$OR$^a$, —SR$^a$, —OR$^a$, C$_{1-6}$alkyl, C$_{1-6}$haloalkyl, —CN, —S(=O)$_n$R$^c$, —O(CH$_2$)$_m$Het, —O(CH$_2$)$_m$C(=O)Het, —O(CH$_2$)$_m$C(=O)NR$^a$R$^a$, —O(CH$_2$)$_m$C(=O)OR$^a$, —O(CH$_2$)$_m$NR$^a$R$^a$, —O(CH$_2$)$_m$OR$^a$, —S(CH$_2$)$_m$Het, —S(CH$_2$)$_m$C(=O)Het, —S(CH$_2$)$_m$C(=O)NR$^a$R$^a$, —S(CH$_2$)$_m$C(=O)OR$^a$, —S(CH$_2$)$_m$NR$^a$R$^3$, —S(CH$_2$)$_m$OR$^a$, —NR$^a$R$^a$, —NHC(=O)R$^a$, —NHC(=O)OR$^a$, N=NR$^a$, NO$_2$, —C(=O)NR$^a$R$^a$, —C(=O)NR$^a$OR$^a$, —C(=O)NR$^a$(R$^b$NR$^a$R$^a$), —C(=O)NR$^a$(R$^b$OR$^a$), —C(=O)NR$^a$(R$^b$S(=O)R$^a$), —C(=O)NR$^a$(R$^b$Het), —C(=O)OR$^a$, —OC(=O)R$^a$, —C(=O)OR$^b$NR$^a$R$^a$, —C(=O)R$^a$, —C(=O)R$^b$NR$^a$R$^a$, —C(=NOR$^a$)R$^a$, —C(=NCN)R$^a$, —S(=O)$_2$NR$^a$R$^a$, —NR$^a$S(=O)$_2$R$^a$, —S(=O)$_2$NR$^a$(R$^b$C(=O)NR$^a$R$^a$), —S(=O)$_2$NR$^a$(R$^b$C(=O)OR$^a$), aminocarbonyl, phenyl, benzyl; or R$^4$ is represented by —(CH$_2$)$_n$R$^5$-Het, —(CH$_2$)$_n$R$^d$, -Het, -Het-Het, R$^5$, —R$^5$-Het, -Het-R$^5$, -Het-OR$^5$, R$^5$—R$^5$, or —R$^5$—OR$^5$; or R$^4$ is represented by C$_{1-6}$alkyl, —NC$_{1-6}$alkyl, or —N(C$_{1-6}$alkyl)$_2$ wherein the C$_{1-6}$alkyl, —NC$_{1-6}$alkyl, —N(C$_{1-6}$alkyl) are substituted by 0, 1 or 2 substituents selected from R$^a$, OR$^a$, halogen or phenyl wherein R$^4$ is not —(CH$_2$)$_z$CH$_3$, —(CH$_2$)$_z$CH$_2$OH, —(CH$_2$)$_z$CO$_2$H, or —(CH$_2$)$_z$CO$_2$C$_{1-6}$alkyl wherein z is 1,2,3,4,5, or 6;

R$^5$ is independently at each instance, phenyl substituted by 0, 1, 2, or 3 groups selected from halogen, C$_{1-6}$haloalkyl, —OC$_{1-6}$haloalkyl, C$_{1-6}$alkyl, —CN, nitro, —OR$^a$, —S(=O)$_n$R$^c$, —O(CH$_2$)$_m$Het, —O(CH$_2$)$_m$C(=O)Het, —O(CH$_2$)$_m$C(=O)NR$^a$R$^a$, —O(CH$_2$)$_m$C(=O)OR$^a$, —O(CH$_2$)$_m$NR$^a$R$^a$, —O(CH$_2$)$_m$OR$^a$, —S(CH$_2$)$_m$Het, —S(CH$_2$)$_m$C(=O)Het, —S(CH$_2$)$_m$C(=O)NR$^a$R$^a$, —S(CH$_2$)$_m$C(=O)OR$^a$, —S(CH$_2$)$_m$NR$^a$R$^a$, —S(CH$_2$)$_m$OR$^6$, —R$^b$OR$^a$, —SR$^a$, —C(=O)NR$^a$R$^a$, —C(=O)NR$^a$OR$^a$, —C(=O)NR$^a$R$^b$NR$^a$R$^a$, —C(=O)NR$^a$R$^b$OR$^a$, —C(=O)NR$^a$R$^b$S(=O)$_n$R$^a$, —C(=O)NR$^a$R$^b$Het, —C(=O)OR$^a$, —OC(=O)R$^a$, —C(=O)OR$^b$NR$^a$R$^a$, C(=O)R$^a$, —C(=O)R$^b$NR$^a$R$^a$, —C(=NOR$^a$)R$^a$, —C(=NCN)R$^a$, —S(=O)$_2$NR$^a$R$^a$, —NR$^a$S(=O)$_2$R$^a$, —S(=O)$_2$NR$^a$R$^b$C(=O)NR$^a$R$^a$, or —S(=O)$_2$NR$^a$R$^b$C(=O)OR$^a$;

R$^a$ is, independently at each instance, H, C$_{1-6}$alkyl, —C(=O)C$_{1-4}$alkyl, C$_{1-4}$haloalkyl, phenyl, benzyl, or 5 or 6-memebered ring, saturated or unsaturated heterocycle containing 1,2,3, or 4 heteroatoms independently selected from N, O or S;

R$^b$ is, independently at each instance, C$_{1-6}$alkyl, —C(=O)C$_{1-4}$alkyl, C$_{1-4}$haloalkyl, phenyl, benzyl, or 5 or 6-memebered ring, saturated or unsaturated heterocycle containing 1,2,3, or 4 heteroatoms independently selected from N, O or S;

R$^c$ is C$_{1-6}$alkyl, C$_{1-4}$haloalkyl, phenyl or benzyl;

R$^d$ is phenyl substituted by 0, 1 or 2 groups selected from —CN, halogen, nitro, C$_{1-6}$alkyl, C$_{1-4}$haloalkyl, —OH, —OR$^c$, —NR$^a$R$^a$, —S(=O)R$^c$, —C(=O)NR$^a$R$^a$, —C(=O)OR$^a$, —NR$^a$C(=O)R$^a$, —OC(=O)R$^a$, B(OH)$_2$, vicinyl —OCH$_2$CH$_2$O—, vicinyl —OC$_{1-2}$haloalkylO—, vicinyl —OCH$_2$O—, vicinyl —CH$_2$OCH$_2$O—, phenyl, benzyl and a 5- or 6-membered ring, saturated or unsaturated heterocycle containing 1, 2, 3 or 4 heteroatoms independently selected from N, O, or S;

m is 1, 2 or 3;

n is 0, 1 or 2;

or a pharmaceutically acceptable salt thereof.

In an additional embodiment the present invention provides compounds having the formula (I) as recited above wherein:

A is N or CR$^{20}$ wherein R$^{20}$ is H, halogen, cyano, C$_{1-6}$alkyl, C$_{1-6}$alkenyl, C$_{1-6}$alkynyl, —OC$_{0-4}$alkyl, —N(C$_{0-4}$ alkyl)(C$_{0-4}$alkyl).

In an additional embodiment the present invention provides compounds having the formula (I) as recited above wherein:

R$^I$ is H, halogen, cyano, nitro, C$_{1-6}$alkyl, C$_{1-6}$alkenyl, C$_{1-6}$alkynyl, S(=O)$_n$C$_{1-4}$alkyl, —S(=O)$_n$N(C$_{1-4}$alkyl)$_n$, —OC$_{0-4}$alkyl, —N(C$_{0-4}$alkyl)(C$_{0-4}$alkyl), —C(=O)OC$_{1-4}$alkyl, —C(=O) C$_{0-4}$alkyl, or —C(=O)N(C$_{0-4}$alkyl)(C$_{0-4}$alkyl) where n is 0, 1 or 2.

In an additional embodiment the present invention provides compounds having the formula (I) as recited above wherein:

R$^{II}$ is H, halogen, cyano, nitro, C$_{1-6}$alkyl, C$_{1-6}$alkenyl, C$_{1-6}$alkynyl, S(=O)$_n$C$_{1-4}$alkyl, —S(=O)$_n$N(C$_{1-4}$alkyl)$_n$, —OC$_{0-4}$alkyl, —N(C$_{0-4}$alkyl)(C$_{0-4}$alkyl), —C(=O)OC$_{1-4}$alkyl, —C(=O) C$_{0-4}$alkyl, or —C(=O)N(C$_{0-4}$alkyl)(C$_{0-4}$alkyl) where n is 0, 1 or 2.

In an additional embodiment the present invention provides compounds having the formula (I) as recited above wherein:

R$^2$ is C$_{1-6}$alkylC$_{3-6}$cycloalkyl or —C$_{1-6}$-alkyl wherein either is optionally substituted with 0, 1, 2 or 3 substituents selected from Het, S(=O)$_n$R$^c$, —S(=O)$_n$NR$^a$R$^a$ halogen, —CN, —OR$^a$, —NR$^a$R$^a$, —C(=O)OR$^a$, —C(=O)R$^a$, —C(=O)NR$^a$R$^a$, —OC(=O)C$_{1-4}$alkyl, or —NR$^a$C(O)C$_{1-4}$alkyl and n is 0, 1 or 2.

In an additional embodiment the present invention provides compounds having the formula (I) as recited above wherein:

R$^3$ is selected from formulas (i), (ii), (iii) or (iv) set forth below:

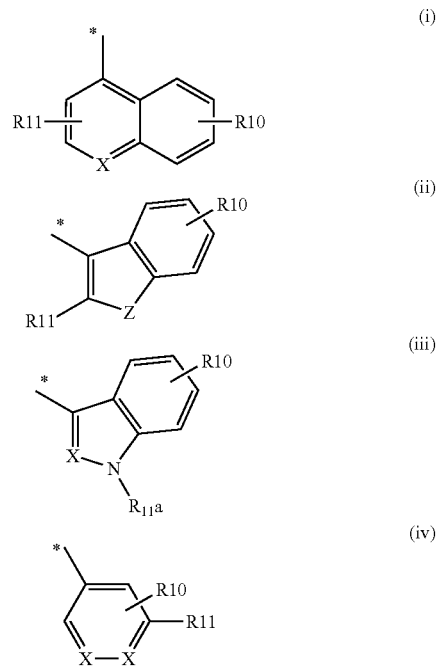

wherein * is the location where (i) or (ii) or (iii) or (iv) is attached to structural formula (I), and X is C or N; and Z is O or S, wherein R$^{10}$ is at any position on the ring and R$^{10}$ and R$^{11}$ are independently at each instance H, R$^a$, halogen, —CN, nitro, OR$^a$, CF$_3$, —NR$^a$R$^a$, —C(=O)OR$^a$, —C(=O)R$^a$, —C(=O)NR$^a$R$^a$, —OC(=O)C$_{1-4}$alkyl, —NR$^a$C(=O)C$_{1-4}$alkyl or —S(=O)$_n$R$^c$; and wherein R$^{11a}$ is R$^a$, —S(=O)$_2$NR$^a$R$^a$ or —S(=O)$_n$R$^c$ and n=1 or 2.
In an additional embodiment the present invention provides compounds having the formula (I) as recited above wherein:
R$^4$ is selected from formulas (a) to (z) or (aa) or (ab) set forth below:
(a)
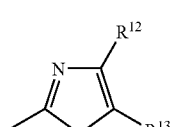
(b)
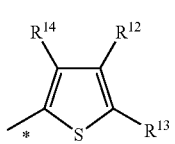
(c)
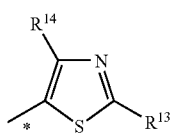
(d)
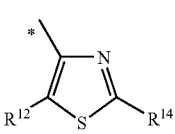
(e)
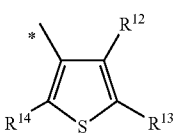
(f)
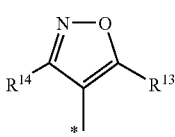
(g)
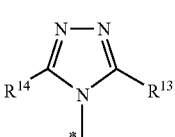
(h)
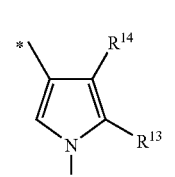
(i)
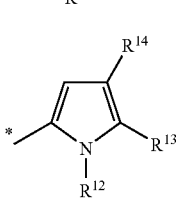
-continued
(j)
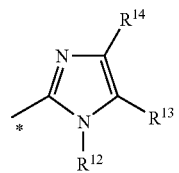
(k)
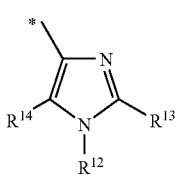
(l)
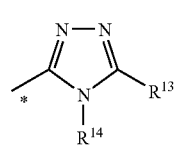
(m)
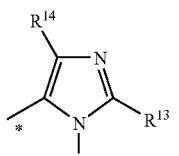
(n)
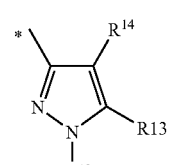
(o)
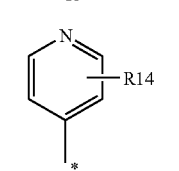
(p)
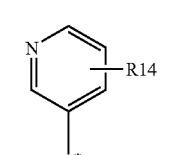
(q)
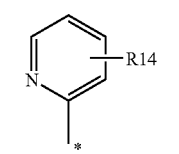
(r)
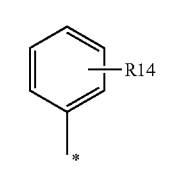

-continued (s)

(t)

(u)

(v)

(w)

(x)

(y)

(z)

(aa)

-continued (ab)

wherein * is the location wherein $R^4$ is attached to the ring system and wherein wherein $R^{12}$, $R^{13}$ and $R^{14}$ are each independently represented by H, Het, $C_{1-6}$alkyl, —CN, —$NR^aR^a$, -nitro, —C(=O)$R^a$, —C(=O)$NR^aR^a$, —C(=O)$NR^aS(=O)_2R^a$, —C(=O)$NR^a$-Het, —C(=O)$NR^aNR^aR^a$, —C(=O)$NR^a(R^bNR^aR^a)$, —C(=O)$NR^a(R^bOR^a)$, —C(=O)$NR^a(R^bS(=O)_2R^a)$, —C(=O)$NR^aR^b$Het, —C(=O)$NR^aOR^a$, —C(=O)$R^bNR^aR^a$, —C(=NOR^a)R^a$, —C(=NCN)$R^a$, —C(=O)$OR^a$, —C(=O)$OR^bNR^aR^a$, —C(=O)$R^a$, —OC(=O)$R^a$, —C(=O)$R^a$—$SR^a$, =S, —$NR^aC(=O)R^a$, —$NR^aC(=O)OR^a$, —$NR^aS(=O)_2R^b$, —C(=NOR^a)$R^a$, —S(=O)$_2R^a$, —S(=O)$_2NR^aR^a$, —S(=O)$_2NR^a(R^bC(=O)NR^aR^a)$, or —S(=O)$_2NR^a(R^bC(=O)OR^a$.

In an additional embodiment the present invention provides compounds having the formula (I) as recited above wherein:

A is N or $CR^{20}$ wherein $R^{20}$ is H, halogen, cyano, $C_{1-6}$allyl, $C_{1-6}$alkenyl, $C_{1-6}$alkynyl, —$OC_{0-4}$alkyl, —N($C_{0-4}$alkyl)($C_{0-4}$alkyl);

$R^I$ is H, halogen, cyano, nitro, $C_{1-6}$alkyl, $C_{1-6}$alkenyl, $C_{1-6}$alkynyl, S(=O)$_n C_{1-4}$alkyl, —S(=O)$_n$N($C_{1-4}$alkyl)$_n$, —$OC_{0-4}$alkyl, —N($C_{0-4}$alkyl)($C_{1-4}$alkyl), —C(=O)$OC_{1-4}$alkyl, —C(=O) $C_{0-4}$alkyl, or —C(=O)N($C_{0-4}$alkyl)($C_{0-4}$alkyl) where n is 0, 1 or 2;

$R^{II}$ is H, halogen, cyano, nitro, $C_{1-6}$alkyl, $C_{1-6}$alkenyl, $C_{1-6}$alkynyl, S(=O)$_n C_{1-4}$alkyl, —S(=O)$_n$N($C_{1-4}$alkyl)$_n$, —$OC_{0-4}$alkyl, —N($C_{0-4}$alkyl)($C_{0-4}$alkyl), —C(=O)$OC_{1-4}$alkyl, —C(=O) $C_{0-4}$alkyl, or —C(=O)N($C_{0-4}$alkyl)($C_{0-4}$alkyl) where n is 0, 1 or 2;

$R^2$ is —$CH_2CH_2CH_3$, —$CH_2$-cyclopropyl, —$CH_2CH$ $(CH_3)_2$, —$CH_2CH_2CH_2F$, —$CH_2$-cyclobutyl, —$CH_2C$ $(CH_3)_3$, —$CH_2CH_2CH(CH_3)_2$, —$CH_2CF_3$, —$CH_2$-methylphenyl, —$CH_2$-phenol, —$CH_2$-(3,5-dimethylisoxazol-4-yl), —$CH_2$—S-phenyl, —$CH_2$-phenylcarboxyl, or —$CH_2SCF_3$;

$R^3$ is selected from formulas (i), (ii), (iii) or (iv) set forth below:

(i)

(ii)

-continued

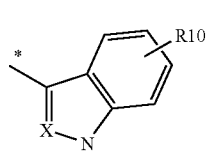
(iii)

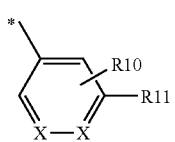
(iv)

wherein * is the location where (i) or (ii) or (iii) or (iv) is attached to structural formula (II), and X is C or N; and Z is O or S, wherein $R^{10}$ is at any position on the ring and $R^{10}$ and $R^{11}$ are independently at each instance H, $R^a$, halogen, —CN, nitro, $OR^a$, $CF_3$, —$NR^aR^a$, —C(=O)$OR^a$, —C(=O)$R^a$, —C(=O)$NR^aR^a$, —OC(=O)$C_{1-4}$alkyl, —$NR^a$C(=O)$C_{1-4}$alkyl or —S(=O)$_nR^c$; and wherein $R^{11a}$ is $R^a$, —S(=O)$_2NR^aR^a$ or —(=O)$_nR^c$ and n=1 or 2;

$R^4$ is selected from formulas (a) to (z) or (aa) or (ab) set forth below:

(a)

(b)

(c)

(d)

(e)

(f)

-continued

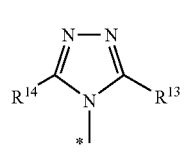
(g)

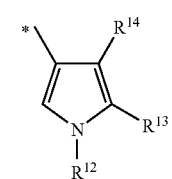
(h)

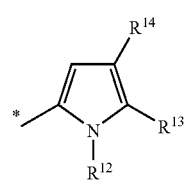
(i)

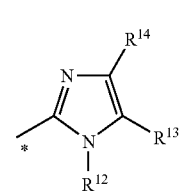
(j)

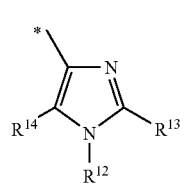
(k)

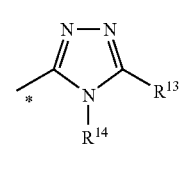
(l)

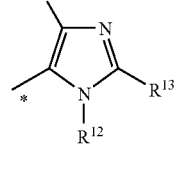
(m)

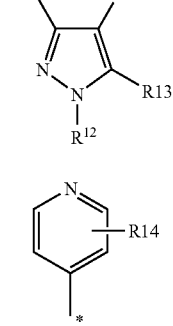
(n)

(o)

-continued (p) 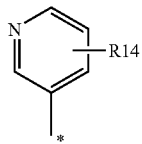

(q) 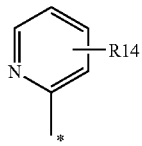

(r) 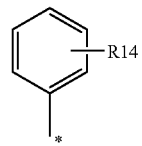

(s) 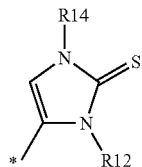

(t) 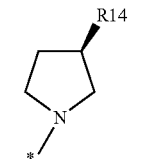

(u) 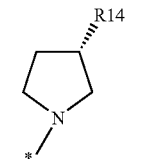

(v) 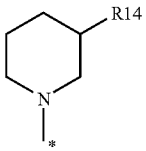

(w) 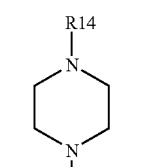

(x) 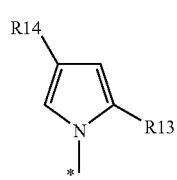

-continued (y) 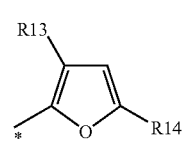

(z) 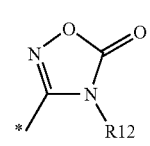

(aa) 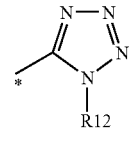

(ab) 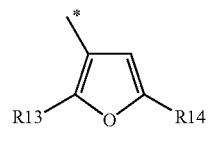

wherein * is the location wherein R⁴ is attached to the ring system and wherein wherein R¹², R¹³ and R¹⁴ are each independently represented by H, Het, C₁₋₆alkyl, —CN, —NRᵃRᵃ, -nitro, —C(=O)Rᵃ, —C(=O)NRᵃRᵃ, —C(=O)NRᵃS(=O)₂Rᵃ, —C(=O)NRᵃ-Het, —C(=O)NRᵃNRᵃRᵃ, —C(=O)NRᵃ(RᵇNRᵃRᵃ), —C(=O)NRᵃ(RᵇORᵃ), —C(=O)NRᵃ(RᵇS(=O)₂Rᵃ), —C(=O)NRᵃRᵇHet, —C(=O)NRᵃORᵃ, —C(=O)RᵇNRᵃRᵃ, —C(=NORᵃ)Rᵃ, —C(=NCN)Rᵃ, —C(=O)ORᵃ, —C(=O)ORᵇNRᵃRᵃ, —C(=O)Rᵃ, —OC(=O)Rᵃ, —C(=O)Rᵃ—SRᵃ, =S, —NRᵃC(=O)Rᵃ, —NRᵃC(=O)ORᵃ, —NRᵃS(=O)₂Rᵇ, —C(=NORᵃ)Rᵃ, —S(=O)₂Rᵃ, —S(=O)₂NRᵃRᵃ, —S(=O)₂NRᵃ(RᵇC(=O)NRᵃRᵃ), or —S(=O)₂NRᵃ(RᵇC(=O)ORᵃ.

In an additional embodiment the present invention provides compounds having the formula (I) as recited above wherein:

5-[8-[(6-chloroquinolin-4-yl)methyl]-6-(cyclopropylmethyl)-5-oxo-6,8-dihydro-5H-pyrazolo[4,3-e][1,2,4]triazolo[4,3-c]pyrimidin-9-yl]-1-methyl-1H-pyrrole-3-carbonitrile;

5-[8-[(6-chloroquinolin-4-yl)methyl]-6-(cyclopropylmethyl)-3-methyl-5-oxo-6,8-dihydro-5H-pyrazolo[4,3-e][1,2,4]triazolo[4,3-c]pyrimidin-9-yl]-1-methyl-1H-pyrrole-3-carbonitrile;

5-[8-[(6-chloroquinolin-4-yl)methyl]-6-(cyclopropylmethyl)-3-(dethylamino)-5-oxo-6,8-dihydro-5H-pyrazolo[4,3-e][1,2,4]triazolo[4,3-c]pyrimidin-9-yl]-1-methyl-1H-pyrrole-3-carbonitrile;

5-[3-amino-8-[(6-chloroquinolin-4-yl)methyl]-6-(cyclopropylmethyl)-5-oxo-6,8-dihydro-5H-pyrazolo[4,3-e][1,2,4]triazolo[4,3-c]pyrimidin-9-yl]-1-methyl-1H-pyrrole-3-carbonitrile;

5-[8-[(6-chloroquinolin-4-yl)methyl]-6-(cyclopropylmethyl)-5-oxo-6,8-dihydro-5H-imidazo[1,2-c]pyrazolo[4,3-e]pyrimidin-9-yl]-1-methyl-1H-pyrrole-3-carbonitrile;

5-[8-[(6-chloroquinolin-4-yl)methyl]-6-(cyclopropylmethyl)-3-methyl-5-oxo-6,8-dihydro-5H-imidazo[1,2-c]pyrazolo[4,3-e]pyrimidin-9-yl]-1-methyl-1H-pyrrole-3-carbonitrile;

8-[(6-chloroquinolin-4-yl)methyl]-6-(cyclopropylmethyl)-9-(1-methyl-1H-imidazol-5-yl)-6,8-dihydro-5H-imidazo[1,2-c]pyrazolo[4,3-e]pyrimidin-5-one;

8-{[5-chloro-1-(methylsulfonyl)-1H-indol-3-yl]methyl}-6-(cyclopropylmethyl)-9-(1-methyl-1H-imidazol-5-yl)-6,8-dihydro-5H-imidazo[1,2-c]pyrazolo[4,3-e]pyrimidin-5-one;

8-[(6-chloroquinolin-4-yl)methyl]-6-(cyclopropylmethyl)-9-[1-methyl-4-(methylsulfonyl)-1H-pyrrol-2-yl]-6,8-dihydro-5H-imidazo[1,2-c]pyrazolo[4,3-e]pyrimidin-5-one;

5-[8-{[5-chloro-1-(methylsulfonyl)-1H-indol-3-yl]methyl}-6-(cyclopropylmethyl)-5-oxo-6,8-dihydro-5H-imidazo[1,2-c]pyrazolo[4,3-e]pyrimidin-9-yl]-1-methyl-1H-pyrrole-3-carbonitrile.

In a further embodiment the present invention provides compounds having the formula (II) as recited above wherein:

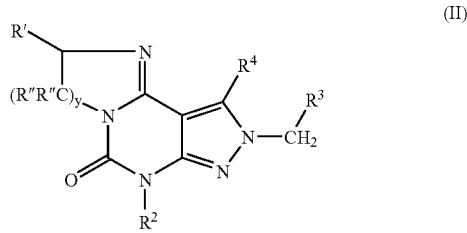

(II)

wherein,

R' is H, optionally substituted alkyl, optionally substituted alkenyl, optionally substituted alkynyl;

R" is independently at each instance H, optionally substituted alkyl, optionally substituted alkenyl, optionally substituted alkynyl;

y is 1 or 2;

$R^2$ is H, optionally substituted alkyl, optionally substituted alkylcycloalkyl, optionally substituted alkenyl, optionally substituted alkynyl, optionally substituted cycloalkyl, optionally substituted cycloalkenyl, optionally substituted cycloalkynyl, optionally substituted aryl, optionally substituted alkoxy, optionally substituted amino, or optionally substituted heterocycle;

$R^3$ is a monocyclic or bicyclic, saturated or unsaturated, ring system comprising 0, 1, 2 or 3 heteroatoms independently selected from N, O, or S, the ring being substituted by 0, 1, 2 or 3 substituents selected from =O, halogen, —$OR^a$, $C_{1-6}$alkyl, $C_{1-6}$haloalkyl, —CN, nitro, —S(=O)$_n R^c$, —O(CH$_2$)$_m$Het, —O(CH$_2$)$_m$C(=O)Het, —O(CH$_2$)$_m$C(=O)NR$^a$R$^a$, —O(CH$_2$)$_m$C(=O)OR$^a$, —O(CH$_2$)$_m$NR$^a$R$^a$, —O(CH$_2$)$_m$OR$^a$, —S(CH$_2$)$_m$Het, —S(CH$_2$)$_m$C(=O)Het, —S(CH$_2$)$_m$C(=O)NR$^a$R$^a$, —S(CH$_2$)$_m$C(=O)OR$^a$, S(CH$_2$)$_m$NR$^a$R$^a$, —S(CH$_2$)$_m$OR$^a$, —NR$^a$R$^a$, —NHC(=O)R$^a$, N=NR$^a$, aminocarbonyl, phenyl, benzyl; or $R^3$ is represented by -Het, -Het-Het, $R^5$, —$R^5$-Het, -Het-$R^5$, -Het-O—$R^5$, —$R^5$—$R^5$, —$R^5$—$OR^5$;

$R^4$ is a monocyclic or bicyclic, saturated or unsaturated, ring system, or a vicinal-fused derivative thereof, which may contain from 5 to 12, preferably 5 to 10, ring atoms, 0, 1, 2, 3 or 4 of which are heteroatoms independently selected from N, O, or S, the ring system being substituted by 0, 1, 2 or 3 substituents selected from B(OH)$_2$, vicinal —OCH$_2$CH$_2$O—, vicinal —OC$_{1-2}$haloalkylO—, vicinal —OCH$_2$O—, vicinal —CH$_2$OCH$_2$O—, =O, halogen, —R$^b$OR$^a$, —SR$^a$, —OR$^a$, C$_{1-6}$alkyl, C$_{1-6}$haloalkyl, —CN, —S(=O)$_n R^c$, —O(CH$_2$)$_m$Het, —O(CH$_2$)$_m$C(=O)Het, —O(CH$_2$)$_m$C(=O)NR$^a$R$^a$, —O(CH$_2$)$_m$C(=O)OR$^a$, —O(CH$_2$)$_m$NR$^a$R$^a$, —O(CH$_2$)$_m$OR$^a$, —S(CH$_2$)$_m$Het, —S(CH$_2$)$_m$C(=O)Het, —S(CH$_2$)$_m$C(=O)NR$^a$R$^a$, —S(CH$_2$)$_m$C(=O)OR$^a$, —S(CH$_2$)$_m$NR$^a$R$^a$, —S(CH$_2$)$_m$OR$^a$, —NR$^a$R$^a$, —NHC(=O)R$^a$, —NHC(=O)OR$^a$, N=NR$^a$, NO$_2$, —C(=O)NR$^a$R$^a$, —C(=O)NR$^a$OR$^a$, —C(=O)NR$^a$(R$^b$NR$^a$R$^a$), —C(=O)NR$^a$(R$^b$OR$^a$), —C(=O)NR$^a$(R$^b$S(=O)$_n R^a$), —C(=O)NR$^a$(R$^b$Het), —C(=O)OR$^a$, —OC(=O)R$^a$, —C(=O)OR$^b$NR$^a$R$^a$, —C(=O)R$^a$, —C(=O)R$^b$NR$^a$R$^a$, —C(=NOR$^a$)R$^a$, —C(=NCN)R$^a$, —S(=O)$_2$NR$^a$R$^a$, —NR$^a$S(=O)$_2$R$^a$, —S(=O)$_2$NR$^a$(R$^b$C(=O)NR$^a$R$^a$), —S(=O)$_2$NR$^a$(R$^b$C(=O)OR$^a$), aminocarbonyl, phenyl, benzyl; or $R^4$ is represented by —(CH$_2$)$_n R^5$-Het, —(CH$_2$)$_n R^d$, -Het, -Het-Het, $R^5$, —$R^5$-Het, -Het-$R^5$, -Het-OR$^5$, $R^5$—$R^5$, or —$R^5$—$OR^5$; or $R^4$ is represented by C$_{1-6}$alkyl, —NC$_{1-6}$alkyl, or —N(C$_{1-6}$alkyl)$_2$ wherein the C$_{1-6}$alkyl, —NC$_{1-6}$alkyl, —N(C$_{1-6}$alkyl) are substituted by 0, 1 or 2 substituents selected from R$^a$, OR$^a$, halogen or phenyl wherein $R^4$ is not —(CH$_2$)$_z$CH$_3$, —(CH$_2$)$_z$CH$_2$OH, —(CH$_2$)$_z$CO$_2$H, or —(CH$_2$)$_z$CO$_2$C$_{1-6}$alkyl wherein z is 1,2,3,4,5, or 6;

$R^5$ is independently at each instance, phenyl substituted by 0, 1, 2, or 3 groups selected from halogen, C$_{1-6}$haloalkyl, —OC$_{1-6}$haloalkyl, C$_{1-6}$alkyl, —CN, nitro, —OR$^a$, —S(=O)$_n R^c$, —O(CH$_2$)$_m$Het, —O(CH$_2$)$_m$C(=O)Het, —O(CH$_2$)$_m$C(=O)NR$^a$R$^a$, —O(CH$_2$)$_m$C(=O)OR$^a$, —O(CH$_2$)$_m$NR$^a$R$^a$, —O(CH$_2$)$_m$OR$^a$, —S(CH$_2$)$_m$Het, —S(CH$_2$)$_m$C(=O)Het, —S(CH$_2$)$_m$C(=O)NR$^a$R$^a$, —S(CH$_2$)$_m$C(=O)OR$^a$, —S(CH$_2$)$_m$NR$^a$R$^a$, —S(CH$_2$)$_m$OR$^a$, —R$^b$OR$^a$, —SR$^a$, —C(=O)NR$^a$R$^a$, —C(=O)NR$^a$OR$^a$, —C(=O)NR$^a$R$^b$NR$^a$R$^a$, —C(=O)NR$^a$R$^b$OR$^a$, —C(=O)NR$^a$R$^b$S(=O)$_n R^a$, —C(=O)NR$^a$R$^b$Het, —C(=O)OR$^a$, —OC(=O)R$^a$, —C(=O)OR$^b$NR$^a$R$^a$, —C(=O)R$^a$, —C(=O)R$^b$NR$^a$R$^a$, —C(=NOR$^a$)R$^a$, —C(=NCN)R$^a$, —S(=O)$_2$NR$^a$R$^a$, —NR$^a$S(=O)$_2$R$^a$, —S(=O)$_2$NR$^a$R$^b$C(=O)NR$^a$R$^a$, or —S(=O)$_2$NR$^a$R$^b$C(=O)OR$^a$;

$R^a$ is, independently at each instance, H, C$_{1-6}$alkyl, —C(=O)C$_{1-4}$alkyl, C$_{1-4}$haloalkyl, phenyl, benzyl, or 5 or 6-memebered ring, saturated or unsaturated heterocycle containing 1,2,3, or 4 heteroatoms independently selected from N, O or S;

$R^b$ is, independently at each instance, C$_{1-6}$alkyl, —C(=O)C$_{1-4}$alkyl, C$_{1-4}$haloalkyl, phenyl, benzyl, or 5 or 6-memebered ring, saturated or unsaturated heterocycle containing 1,2,3, or 4 heteroatoms independently selected from N, O or S;

$R^c$ is C$_{1-6}$alkyl, C$_{1-4}$haloalkyl, phenyl or benzyl;

$R^d$ is phenyl substituted by 0, 1 or 2 groups selected from —CN, halogen, nitro, C$_{1-6}$alkyl, C$_{1-4}$haloalkyl, —OH, —OR$^c$, —NR$^a$R$^a$, —S(=O)$_n R^c$, —C(=O)NR$^a$R$^a$, —C(=O)OR$^a$, —NR$^a$C(=O)R$^a$, —OC(=O)R$^a$, B(OH)$_2$, vicinyl —OCH$_2$CH$_2$O—, vicinyl —OC$_{1-2}$haloalkylO—, vicinyl —OCH$_2$O—, vicinyl —CH$_2$OCH$_2$O—, phenyl, benzyl and a 5- or 6-membered ring, saturated or unsaturated heterocycle containing 1, 2, 3 or 4 heteroatoms independently selected from N, O, or S;

m is 1, 2 or 3;

n is 0, 1 or 2;

or a pharmaceutically acceptable salt thereof.

In an additional embodiment the present invention provides compounds having the formula (II) as recited above wherein:

R' is H, C$_{1-6}$alkyl, C$_{1-6}$alkenyl, C$_{1-6}$alkynyl.

In an additional embodiment the present invention provides compounds having the formula (II) as recited above wherein:

R" is independently at each instance H, $C_{1-6}$allyl, $C_{1-6}$alkenyl, $C_{1-6}$alkynyl.

In an additional embodiment the present invention provides compounds having the formula (II) as recited above wherein:

$R^2$ is $C_{1-6}$alkyl$C_{3-6}$cycloalkyl or —$C_{1-12}$alkyl wherein either is optionally substituted with 0, 1, 2 or 3 substituents selected from Het, $S(=O)_nR^c$, —$S(=O)_nNR^aR^a$ halogen, —CN, —$OR^a$, —$NR^aR^a$, —$C(=O)OR^a$, —$C(=O)R^a$, —$C(=O)NR^aR^a$, —$OC(=O)C_{1-4}$alkyl, or —$NR^aC(=O)$ $C_{1-4}$alkyl and n is 0, 1 or 2.

In an additional embodiment the present invention provides compounds having the formula (II) as recited above wherein:

$R^3$ is selected from formulas (i), (ii), (iii) or (iv) set forth below:

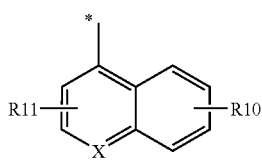
(i)

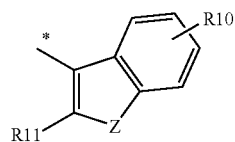
(ii)

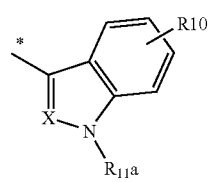
(iii)

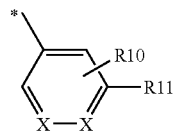
(iv)

wherein * is the location where (i) or (ii) or (iii) or (iv) is attached to structural formula (I), and X is C or N; and Z is O or S, wherein $R^{10}$ is at any position on the ring and $R^{10}$ and $R^{11}$ are independently at each instance H, $R^a$, halogen, —CN, nitro, $OR^a$, $CF_3$, —$NR^aR^a$, —$C(=O)OR^a$, —$C(=O)R^a$, —$C(=O)NR^aR^a$, —$OC(=O)C_{1-4}$alkyl, —$NR^aC(=O)C_{1-4}$alkyl or —$S(=O)_nR^c$; and wherein $R^{11a}$ is $R^a$, —$S(=O)_2NR^aR^a$ or —$S(O)_nR^c$ and n=1 or 2.

In an additional embodiment the present invention provides compounds having the formula (II) as recited above wherein:

$R^4$ is selected from formulas (a) to (z) or (aa) or (ab) set forth below:

(a)

(b)

(c)

(d)

(e)

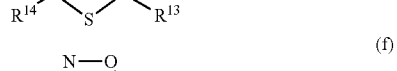
(f)

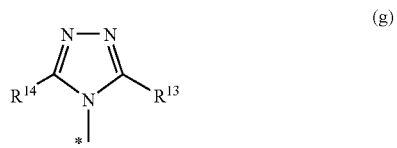
(g)

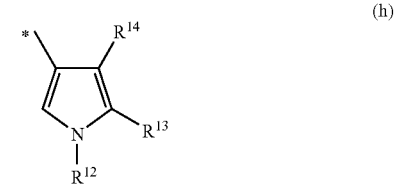
(h)

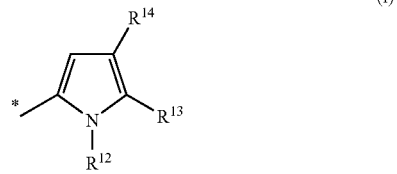
(i)

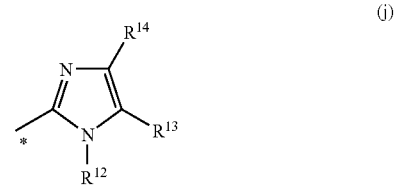
(j)

-continued
(k) 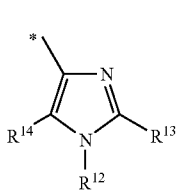
(l) 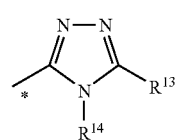
(m) 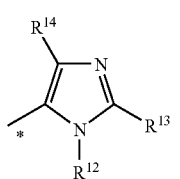
(n) 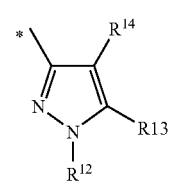
(o) 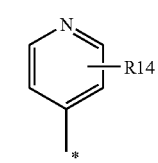
(p) 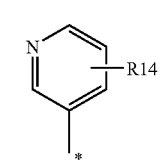
(q) 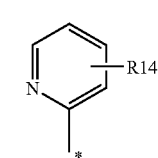
(r) 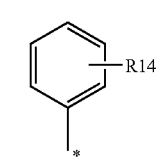
(s) 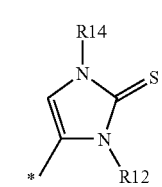
-continued
(t) 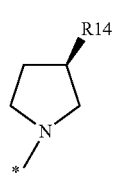
(u) 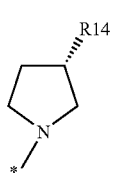
(v) 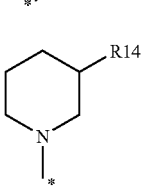
(w) 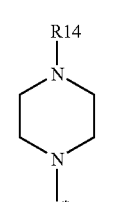
(x) 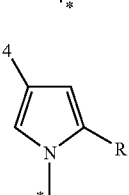
(y) 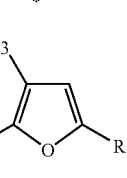
(z) 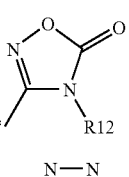
(aa) 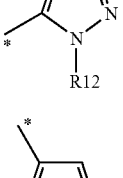
(ab) 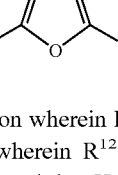
wherein * is the location wherein $R^4$ is attached to the ring system and wherein wherein $R^{12}$, $R^{13}$ and $R^{14}$ are each independently represented by H, Het, $C_{1-6}$alkyl, —CN, —NR$^a$R$^a$, -nitro, —C(=O)R$^a$, —C(O)NR$^a$R$^a$, —C(=O)

NR$^a$S(=O)$_2$R$^a$, —C(=O)NR$^a$-Het, —C(=O)NR$^a$NR$^a$R$^a$, —C(=O)NR$^a$(R$^b$NR$^a$R$^a$), —C(=O)NR$^a$(R$^b$OR$^a$), —C(=O)NR$^a$(R$^b$S(=O)$_2$R$^a$), —C(=O)NR$^a$R$^b$Het, —C(=O)NR$^a$OR$^a$, —C(=O)R$^b$NR$^a$R$^a$, —C(=NOR$^a$)R$^a$, —C(=NCN)R$^a$, —C(=O)OR$^a$, —C(=O)OR$^b$NR$^a$R$^a$, —C(=O)R$^a$, —OC(=O)R$^a$, —C(=O)R$^a$—SR$^a$, =S, —NR$^a$C(=O)R$^a$, —NR$^a$C(=O)OR$^a$, —NR$^a$S(=O)$_2$R$^b$, —C(=NOR$^a$)R$^a$, —S(=O)$_2$R$^a$, —S(=O)$_2$NR$^a$R$^a$, —S(=O)$_2$NR$^a$(R$^b$C(=O)NR$^a$R$^a$), or —S(=O)$_2$NR$^a$(R$^b$C(=O)OR$^a$.

In an additional embodiment the present invention provides compounds having the formula (II) as recited above wherein:

R' is H, C$_{1-6}$alkyl, C$_{1-6}$alkenyl, C$_{1-6}$alkynyl;

R" is independently at each instance H, C$_{1-6}$alkyl, C$_{1-6}$alkenyl, C$_{1-6}$alkenyl;

y is 1;

R$^2$ is —CH$_2$CH$_2$CH$_3$, —CH$_2$-cyclopropyl, —CH$_2$CH(CH$_3$)$_2$, —CH$_2$CH$_2$CH$_2$F, —CH$_2$-cyclobutyl, —CH$_2$C(CH$_3$)$_3$, —CH$_2$CH$_2$CH(CH$_3$)$_2$, —CH$_2$CF$_3$, —CH$_2$-methylphenyl, —CH$_2$-phenol, —CH$_2$-(3,5-dimethylisoxazol-4-yl), —CH$_2$—S-phenyl, —CH$_2$-phenylcarboxyl, or —CH$_2$SCF$_3$;

R$^3$ is selected from formulas (i), (ii), (iii) or (iv) set forth below:

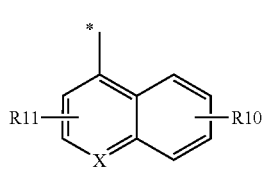
(i)

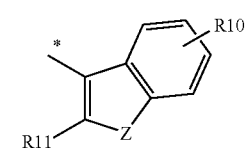
(ii)

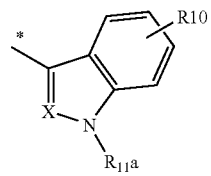
(iii)

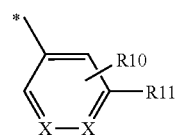
(iv)

wherein * is the location where (i) or (ii) or (iii) or (iv) is attached to structural formula (I), and X is C or N; and Z is O or S, wherein R$^{10}$ is at any position on the ring and R$^{10}$ and R$^{11}$ are independently at each instance H, R$^a$, halogen, —CN, nitro, OR$^a$, CF$_3$, —NR$^a$R$^a$, —C(=O)OR$^a$, —C(=O)R$^a$, —C(=O)NR$^a$R$^a$, —OC(=O)C$_{1-4}$alkyl, —NR$^a$C(=O)C$_{1-4}$allyl or —S(=O)$_n$R$^c$; and wherein R$^{11a}$ is R$^a$, —S(=O)$_2$NR$^a$R$^a$ or —S(=O)$_n$R$^c$ and n=1 or 2;

R$^4$ is selected from formulas (a) to (z) or (aa) or (ab) set forth below:

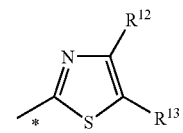
(a)

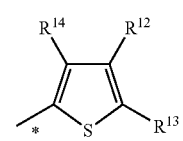
(b)

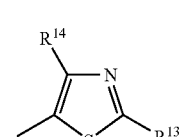
(c)

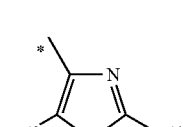
(d)

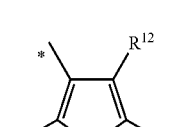
(e)

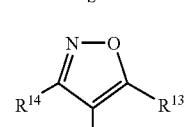
(f)

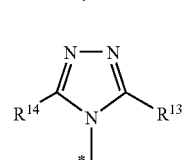
(g)

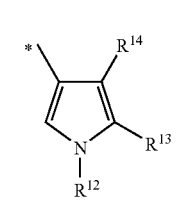
(h)

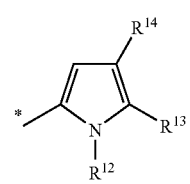
(i)

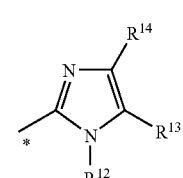
(j)

-continued
(k) 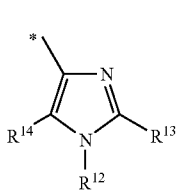
(l) 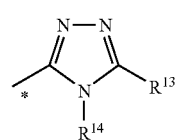
(m) 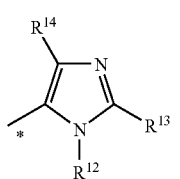
(n) 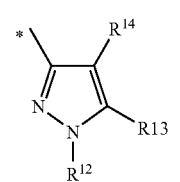
(o) 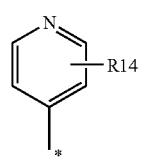
(p) 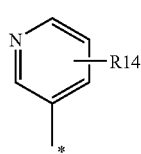
(q) 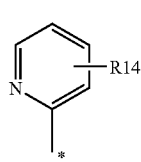
(r) 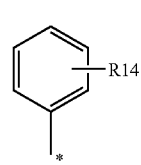
(s) 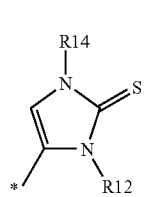
-continued
(t) 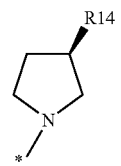
(u) 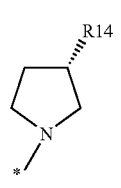
(v) 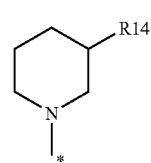
(w) 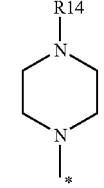
(x) 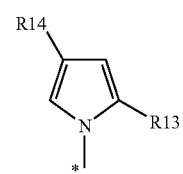
(y) 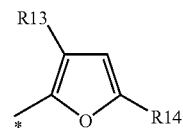
(z) 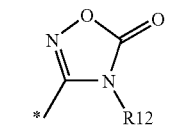
(aa) 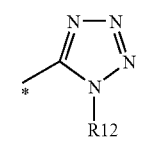
(ab) 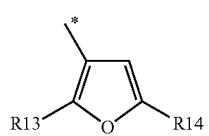
wherein * is the location wherein $R^4$ is attached to the ring system and wherein wherein $R^{12}$, $R^{13}$ and $R^{14}$ are each independently represented by H, Het, $C_{1-6}$alkyl, —CN, —NR$^a$R$^a$, -nitro, —C(=O)R$^a$, —C(=O)NR$^a$R$^a$, —C(=O)

NR$^a$S(=O)$_2$R$^a$, —C(=O)NR$^a$-Het, —C(=O)NR$^a$NR$^a$R$^a$, —C(=O)NR$^a$(R$^b$NR$^a$R$^a$), —C(=O)NR$^a$(R$^b$OR$^a$), —C(=O)NR$^a$(R$^b$S(=O)$_2$R$^a$), —C(=O)NR$^a$R$^b$Het, —C(=O)NR$^a$OR$^a$, —C(=O)R$^b$NR$^a$R$^a$, —C(=NOR$^a$)R$^a$, —C(=NCN)R$^a$, —C(=O)OR$^a$, —C(=O)OR$^b$NR$^a$R$^a$, —C(=O)R$^a$, —OC(=O)R$^a$, —C(=O)R$^a$—SR$^a$, =S, —NR$^a$C(=O)R$^a$, —NR$^a$C(=O)OR$^a$, —NR$^a$S(=O)$_2$R$^b$, —C(=NOR$^a$)R$^a$, —S(=O)$_2$R$^a$, —S(=O)$_2$NR$^a$R$^a$, —S(=O)$_2$NR$^a$(R$^b$C(=O)NR$^a$R$^a$), or —S(=O)$_2$NR$^a$(R$^b$C(=O)OR$^a$.

In an additional embodiment the present invention provides compounds having the formula (II) as recited above wherein:

5-{8-[(6-chloroquinolin-4-yl)methyl]-6-isobutyl-5-oxo-2,5, 6,8-tetrahydro-3H-imidazo [1,2-c]pyrazolo[4,3-e]pyrimidin-9-yl}-1-methyl-1H-pyrrole-3-carbonitrile;5-{8-[(6-chloroquinolin-4-yl)methyl]-6-isobutyl-5-oxo-2,5,6,8-tetrahydro-3H-imidazo[1,2-c]pyrazolo[4,3-e]pyrimidin-9-yl}-1-methyl-1H-pyrrole-3-carbonitrile;

5-[8-[(6-chloroquinolin-4-yl)methyl]-6-(cyclopropylmethyl)-3-methyl-5-oxo-2,5,6,8-tetrahydro-3H-imidazo[1,2-c]pyrazolo[4,3-e]pyrimidin-9-yl]-1-methyl-1H-pyrrole-3-carbonitrile;

5-[8-[(6-chloroquinolin-4-yl)methyl]-6-(cyclopropylmethyl)-2-methyl-5-oxo-2,5,6,8-tetrahydro-3H-imidazo[1,2-c]pyrazolo[4,3-e]pyrimidin-9-yl]-1-methyl-1H-pyrrole-3-carbonitrile;

5-[(3R)-8-[(6-chloroquinolin-4-yl)methyl]-6-(cyclopropylmethyl)-3-methyl-5-oxo-2,5,6,8-tetrahydro-3H-imidazo [1,2-c]pyrazolo[4,3-e]pyrimidin-9-yl]-1-methyl-1H-pyrrole-3-carbonitrile;

5-[(3S)-8-[(6-chloroquinolin-4-yl)methyl]-6-(cyclopropylmethyl)-3-methyl-5-oxo-2,5,6,8-tetrahydro-3H-imidazo [1,2-c]pyrazolo[4,3-e]pyrimidin-9-yl]-1-methyl-1H-pyrrole-3-carbonitrile;

5-[9-[(6-chloroquinolin-4-yl)methyl]-7-(cyclopropylmethyl)-6-oxo-2,3,4,6,7,9-hexahydropyrazolo[4,3-e]pyrimido[1,2-c]pyrimidin-10-yl]-1-methyl-1H-pyrrole-3-carbonitrile.

In an additional embodiment the present invention provides compounds having the formula (I) or (II) as recited above for use as a medicament.

In an additional embodiment the present invention provides the use of a compound having the formula (I) or (II) in the manufacture of a medicament for the treatment or prophylaxis of disorders associated with *H. pylori* infection.

In an additional embodiment the present invention provides a method for the treatment of infections associated with *H. pylori* comprising administering to a host in need of such treatment a therapeutically effective amount of a compound as defined in formula (I) or (II).

In an additional embodiment the present invention provides a method for the prophylaxis treatment of infections associated with *H. pylori* comprising administering to a host in need of such treatment a therapeutically effective amount of a compound as defined in formula (I) or (II).

In an additional embodiment the present invention provides a method for the treatment or prophylaxis of infections associated with *H. pylori* comprising administering to a host in need of such treatment a therapeutically effective amount of a compound as defined in formula (I) or (II).

In an additional embodiment the present invention provides a pharmaceutical composition comprising a compound as defined in formula (I) or (II) together with at least one pharmaceutically acceptable carrier, diluent or excipient.

Definitions

The definitions set forth in this section are intended to clarify terms used throughout this application. The term "herein" means the entire application.

As used in this application, the term "optionally substituted," as used herein, means that substitution is optional and therefore it is possible for the designated atom to be unsubstituted. In the event a substitution is desired then such substitution means that any number of hydrogens on the designated atom is replaced with a selection from the indicated group, provided that the designated atom's normal valency is not exceeded, and that the substitution results in a stable compound. For example when a substituent is keto (i.e., =O), then 2 hydrogens on the atom are replaced.

When any variable (e.g., $R^1$, $R^4$, $R^a$, $R^e$ etc.) occurs more than one time in any constituent or formula for a compound, its definition at each occurrence is independent of its definition at every other occurrence. Thus, for example, if a group is shown to be substituted with 0-3 $R^1$, then said group may optionally be substituted with 0,1, 2 or 3 $R^1$ groups and $R^e$ at each occurrence is selected independently from the definition of $R^e$. Also, combinations of substituents and/or variables are permissible only if such combinations result in stable compounds.

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. When required, separation of the racemic material can be achieved by methods known in the art. Many geometric isomers of olefins, C—N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein "acyl" refers to groups of the of the general formula —C(=O)—R, wherein R is hydrogen, hydrocarbyl radical, amino or alkoxy. Examples of acyl groups include, but are not limited to acetyl, propionyl, benzoyl, phenyl acetyl, carboethoxy, and dimethylcarbamoyl.

As used herein the term "amine" or "amino" refers to groups of the general formula —NRR', wherein R and R' are independently selected from hydrogen or a hydrocarbyl radical.

As used herein "aromatic" refers to hydrocarbyl groups having one or more polyunsaturated carbon rings having aromatic character, (e.g., 4n+2 delocalized electrons) and comprising up to about 14 carbon atoms.

As used herein, "allyl" or "alkylene" used alone or as a suffix or prefix, is intended to include both branched and straight-chain saturated aliphatic hydrocarbon groups having from 1 to 12 carbon atoms or if a specified number of carbon atoms is provided then that specific number would be intended. For example "$C_{1-6}$ alkyl" denotes alkyl having 1, 2, 3, 4, 5 or 6 carbon atoms. Examples of alkyl include, but are not limited to, methyl, ethyl, n-propyl, i-propyl, n-butyl, i-butyl, sec-butyl, t-butyl, pentyl, and hexyl. As used herein, "$C_{1-3}$ alkyl", whether a terminal substituent or an alkylene group linking two substituents, is understood to specifically include both branched and straight-chain methyl, ethyl, and propyl.

As used herein, "alkenyl" or "alkenylene" is intended to include from 2 to 12 hydrocarbon atoms of either a straight or branched configuration with one or more carbon-carbon double bonds that may occur at any stable point along the chain. Examples of "$C_{3-6}$alkenyl" include, but are not limited to, 1-propenyl, 2-propenyl, 1-butenyl, 2-butenyl, 3-butenyl, 3-methyl-2-butenyl, 2-pentenyl, 3-pentenyl, hexenyl.

As used herein, "alkynyl" or "alkynylene" is intended to include from 2 to 12 hydrocarbon chains of either a straight or branched configuration with one or more carbon-carbon triple bonds that may occur at any stable point along the chain. Examples of alkynyl include but are not limited to ethynyl, 1-propynyl, 2-propynyl, 1-butynyl, 2-butynyl, 3-butynyl.

As used herein, "alkoxy" or "alkyloxy" represents an alkyl group as defined above with the indicated number of carbon atoms attached through an oxygen bridge. Examples of alkoxy include, but are not limited to, methoxy, ethoxy, n-propoxy, isopropoxy, n-butoxy, isobutoxy, t-butoxy, n-pentoxy, isopentoxy, cyclopropylmethoxy, allyloxy and propargyloxy. Similarly, "alkylthio" or "thioalkoxy" represent an alkyl group as defined above with the indicated number of carbon atoms attached through a sulphur bridge.

As used herein, the term "aryl" is intended to mean aromatic groups including both monocyclic aromatic groups comprising 6 carbon atoms and polycyclic aromatic groups comprising up to about 14 carbon atoms.

As used herein the term "cycloalkyl" is intended to include saturated ring groups, having the specified number of carbon atoms. For example, "$C_{3-6}$ cycloalkyl" denotes such groups as cyclopropyl, cyclobutyl, cyclopentyl, or cyclohexyl.

As used herein the term "alkylcycloalkyl" is intended to mean an alkyl attached to the formula atom and also attached to a cycloalkyl. Examples of alkylcycloalkyl include, but are not limited to cyclopropylmethyl, cyclopentylmethyl, cyclohexylmethyl, cycloheptylmethyl, cyclopropylethyl, cyclopentylethyl, cyclohexylethyl, cycloheptylethyl, cyclopropylpropyl, cyclopentylpropyl, cyclohexylpropyl, cycloheptylpropyl.

As used herein "cycloalkenyl" refers to ring-containing hydrocarbyl groups having at least one carbon-carbon double bond in the ring, and having from 3 to 12 carbons atoms.

As used herein "cycloalkynyl" refers to ring-containing hydrocarbyl groups having at least one carbon-carbon triple bond in the ring, and having from 7 to 12 carbons atoms.

As used herein, "electronically neutral" refers to a stable compound having a no charge.

As used herein, "halo" or "halogen" refers to fluoro, chloro, bromo, and iodo. "Counterion" is used to represent a small, negatively charged species such as chloride, bromide, hydroxide, acetate, sulfate, tosylate, benezensulfonate, and the like.

As used herein, "haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, pentachloroethyl, 2,2,2-trifluoroethyl, 2,2-difluoroethyl, heptafluoropropyl, and heptachloropropyl. "Haloalkoxy" is intended to mean a haloalkyl group as defined above with the indicated number of carbon atoms attached through an oxygen bridge; for example trifluoromethoxy, pentafluoroethoxy, 2,2,2-trifluoroethoxy, and the like. "Haloalkylthio" is intended to mean a haloalkyl group as defined above with the indicated number of carbon atoms attached through a sulphur bridge.

As used herein, the term "Het" is intended to mean a 5 or 6 member ring, saturated or unsaturated heterocycle containing 1, 2, 3 or 4 heteroatoms independently selected from N, O, or S, and substituted by 0, 1, 2 or 3 substituents selected from halogen, $C_{1-4}$alkyl, —S(=O)$_n$R$^c$, —C(=O)R$^a$, or —S(=O)$_2$NR$^a$R$^a$, vicinal —OCH$_2$CH$_2$O—, vicinal —OC$_{1-2}$haloalkylO—, vicinal —OCH$_2$O—, or vicinal —CH$_2$OCH$_2$O—, =O, halogen, cyano, —R$^b$OR$^a$, —R$^b$SR$^a$, —SR$^a$, —OR$^a$, $C_{1-6}$alkyl, $C_{1-6}$haloalkyl, —CN, nitro, —OH, 'NHR$^a$, —NR$^a_2$, —NHC(=O)R$^a$, N=NR$^a$, —C(=O)NR$^a$R$^a$, —C(=O)NR$^a$OR$^a$, —C(=O)NR$^a$R$^b$NR$^a$R$^a$, —C(=O)NR$^a$R$^b$OR$^a$, C(=O)NR$^a$R$^b$S(=O)$_n$R$^a$, —C(=O)NR$^2$R$^b$Het, —C(=O)OR$^a$, —OC(=O)R$^a$, —C(=O)OR$^b$NR$^a$R$^a$, —C(=O)R$^b$NR$^a$R$^a$, —C(=NOR$^a$)R$^a$, —C(=NCN)R$^a$, —NR$^a$S(=O)$_2$R$^a$, —S(=O)$_2$NR$^a$R$^b$C(=O)NR$^a$R$^a$, or —S(=O)$_2$NR$^a$R$^b$C(=O)OR$^a$;

As used herein, the term "heterocycle" or "heterocyclic" refers to a ring-containing monovalent and divalent structures having one or more heteroatoms, independently selected from N, O and S, as part of the ring structure and comprising from 3 to 20 atoms in the rings. Heterocyclic groups may be saturated or unsaturated, containing one or more double bonds, and heterocyclic groups may contain more that one ring. The heterocyclic rings described herein may be substituted on carbon or on a heteroatom atom if the resulting compound is stable. If specifically noted, nitrogen in the heterocycle may optionally be quaternized. It is understood that when the total number of S and O atoms in the heterocycle exceeds 1, then these heteroatoms are not adjacent to one another.

Examples of heterocycles include, but are not limited to, 1H-indazole, 2-pyrrolidonyl, 2H, 6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azetidine, aziridine, azocinyl, benzimidazolyl, benzofuranyl, benzothiofuranyl, benzothiophenyl, benzoxazolyl, benzthiazolyl, benzotriazolyl, benzotetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dioxolane, furyl, 2,3-dihydrofuran, 2,5-dihydrofuran, dihydrofuro[2,3-b]tetrahydrofuran, furanyl, furazanyl, homopiperidinyl, imidazolidine, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxirane, oxazolidinylperimidinyl, phenanthridinyl, phenanthrolinyl, phenarsazinyl, phenazinyl, phenothiazinyl, phenothiazinyl, phenoxazinyl, phthalazinyl, piperazinyl, piperidinyl, pteridinyl, piperidonyl, 4-piperidonyl, purinyl, pyranyl, pyrrolidine, pyrroline, pyrrolidine, pyrazinyl, pyrazolidinyl, pyrazolinyl, pyrazolyl, pyridazinyl, pyridooxazole, pyridoimidazole, pyridothiazole, pyridinyl, N-oxide-pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, thiophane, thiotetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, thiamine, triazinyl, 1,2,3-triazolyl, 1,2,4-triazolyl, 1,2,5-triazolyl, 1,3,4-triazolyl, xanthenyl.

In addition to the polycyclic heterocycles described above, heterocyclic or heterocycle compounds include polycyclic heterocyclic moieties wherein the ring fusion between two or more rings comprises more than one bond common to both rings and more than two atoms common to both rings. Examples of such bridged heterocycles include quinuclidine, diazabicyclo[2.2.1]heptane and 7-oxabicyclo[2.2.1]heptane.

As used herein, "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, maleic, tartaric, citric, ascorbic, palmitic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is hereby incorporated by reference.

"Prodrugs" are intended to include any covalently bonded carriers that release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of formula (I), and the like.

"Stable compound" and "stable structure" are meant to indicate a compound that is sufficiently robust to survive isolation to a useful degree of purity from a reaction mixture, and formulation into an efficacious therapeutic agent.

Formulations

Compounds of the present invention may be administered orally, parenteral, buccal, vaginal, rectal, inhalation, insufflation, sublingually, intramuscularly, subcutaneously, topically, intranasally, intraperitoneally, intrathoracially, intravenously, epidurally, intrathecally, intracerebroventricularly and by injection into the joints.

The dosage will depend on the route of administration, the severity of the disease, age and weight of the patient and other factors normally considered by the attending physician, when determining the individual regimen and dosage level as the most appropriate for a particular patient.

An effective amount of a compound of the present invention for use in therapy of infection is an amount sufficient to symptomatically relieve in a warm-blooded animal, particularly a human the symptoms of infection, to slow the progression of infection, or to reduce in patients with symptoms of infection the risk of getting worse.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances, which may also act as diluents, flavoring agents, solubilizers, lubricants, suspending agents, binders, or tablet disintegrating agents; it can also be an encapsulating material.

In powders, the carrier is a finely divided solid, which is in a mixture with the finely divided active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized molds anial-lowed to cool and solidify.

Suitable carriers include magnesium carbonate, magnesium stearate, talc, lactose, sugar, pectin, dextrin, starch, tragacanth, methyl cellulose, sodium carboxymethyl cellulose, a low-melting wax, cocoa butter, and the like.

Some of the compounds of the present invention are capable of forming salts with various inorganic and organic acids and bases and such salts are also within the scope of this invention. Examples of such acid addition salts include acetate, adipate, ascorbate, benzoate, benzenesulfonate, bicarbonate, bisulfate, butyrate, camphorate, camphorsulfonate, choline, citrate, cyclohexyl sulfamate, diethylenediamine, ethanesulfonate, fumarate, glutamate, glycolate, hemisulfate, 2-hydroxyethylsulfonate, heptanoate, hexanoate, hydrochloride, hydrobromide, hydroiodide, hydroxymaleate, lactate, malate, maleate, methanesulfonate, meglumine, 2-naphthalenesulfonate, nitrate, oxalate, pamoate, persulfate, phosphate, diphosphate, picrate, pivalate, propionate, quinate, salicylate, stearate, succinate, sulfamate, sulfanilate, sulfate, tartrate, tosylate (p-toluenesulfonate), trifluoroacetate, and undecanoate. Base salts include ammonium salts, alkali metal salts such as sodium, lithium and potassium salts, alkaline earth metal salts such as aluminum, calcium and magnesium salts, salts with organic bases such as dicyclohexylamine salts, N-methyl-D-glucamine, and salts with amino acids such as arginine, lysine, ornithine, and so forth. Also, basic nitrogen-containing groups may be quaternized with such agents as: lower alkyl halides, such as methyl, ethyl, propyl, and butyl halides; dialkyl sulfates like dimethyl, diethyl, dibutyl; diamyl sulfates; long chain halides such as decyl, lauryl, myristyl and stearyl halides; aralkyl halides like benzyl bromide and others. Non-toxic physiologically-acceptable salts are preferred, although other salts are also useful, such as in isolating or purifying the product.

The salts may be formed by conventional means, such as by reacting the free base form of the product with one or more equivalents of the appropriate acid in a solvent or medium in which-the salt is insoluble, or in a solvent such as water, which is removed in vacuo or by freeze drying or by exchanging the anions of an existing salt for another anion on a suitable ion-exchange resin.

In order to use a compound of the formula (I) or a pharmaceutically acceptable salt thereof for the therapeutic treatment (including prophylactic treatment) of mammals including humans, it is normally formulated in accordance with standard pharmaceutical practice as a pharmaceutical composition.

In addition to the compounds of the present invention, the pharmaceutical composition of this invention may also contain, or be co-administered (simultaneously or sequentially) with, one or more pharmacological agents of value in treating one or more disease conditions referred to herein.

The term composition is intended to include the formulation of the active component or a pharmaceutically acceptable salt with a pharmaceutically acceptable carrier. For example this invention may be formulated by means known in the art into the form of, for example, tablets, capsules, aqueous or oily solutions, suspensions, emulsions, creams, ointments, gels, nasal sprays, suppositories, finely divided powders or aerosols or nebulisers for inhalation, and for parenteral use (including intravenous, intramuscular or infusion) sterile aqueous or oily solutions or suspensions or sterile emulsions.

Liquid form compositions include solutions, suspensions, and emulsions. Sterile water or water-propylene glycol solutions of the active compounds may be mentioned as an example of liquid preparations suitable for parenteral administration. Liquid compositions can also be formulated in solution in aqueous polyethylene glycol solution. Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

The pharmaceutical compositions can be in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Such methods include, but are not limited to, those described below. All references cited herein are hereby incorporated in their entirety by reference.

The novel compounds of this invention may be prepared using the reactions and techniques described herein. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents, which are compatible with the reaction conditions, will be readily apparent to one skilled in the art and alternate methods must then be used.

Examples of such processes are illustrated below:

In an aspect of the invention, intermediate compounds of formula Ib may be formed by reacting compounds of formula Ia with $R^2$—X in a solvent such as DMSO and a base such as $K_2CO_3$ with heat as set forth below:

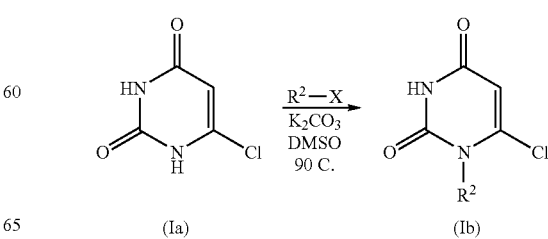

An intermediate compound of formula Ic may be formed by reacting a compound of Formula Ib with $NH_2NH_2H_2O$ in ethanol and refluxed as follows:

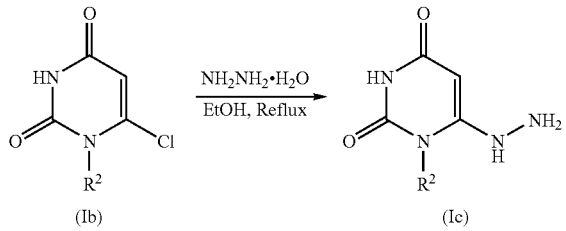

Intermediate compound of Formula Id may be formed by reacting compounds of formula Ic with $R^3$—CHO in methanol as follows:

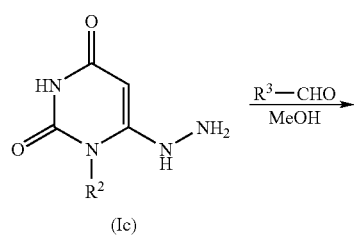

Intermediate compounds of formula Ie may by formed by reacting compounds of formula Id with $R^4$—CHO and reflux in DMF with piperdine as follows:

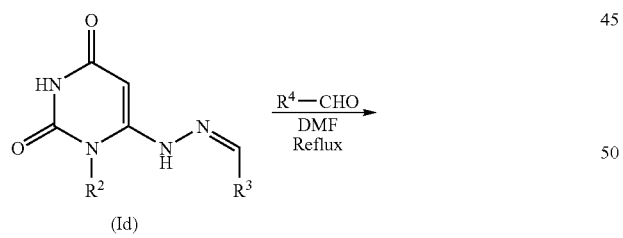

Compounds of formula If may by formed by reacting compounds of formula Ie with $POCl_3$, 3-nitro-1,2,4 triazole in pyridine at 70 C followed by amine ($HORNH_2$) as set forth below:

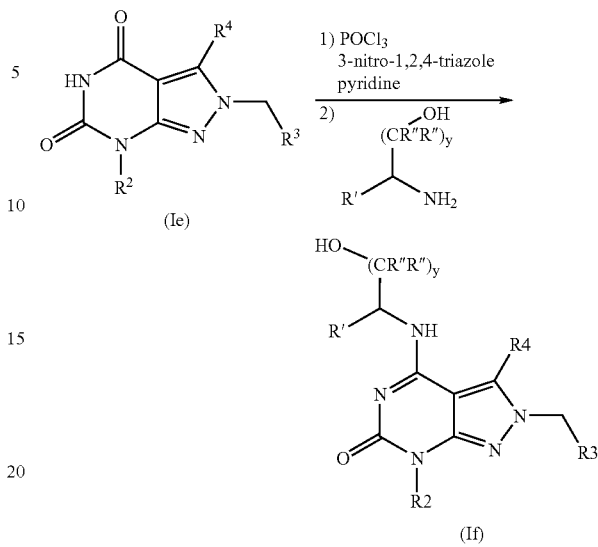

Compounds of formula I may by formed by reacting compounds of formula If with methanesulfonyl chloride as set forth below:

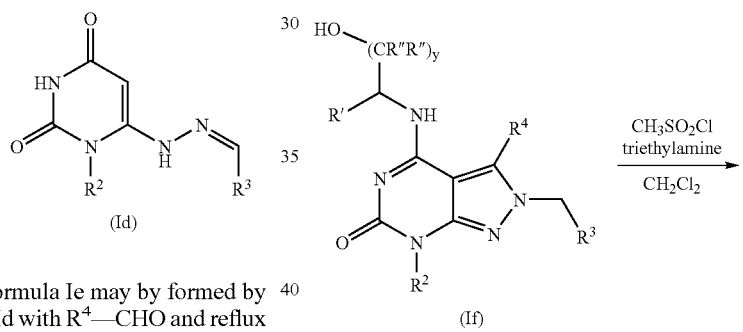

In an aspect of the invention, intermediate compounds of formula IIa may be formed from reaction of compounds of formula Ie with $P_2S_5$ in pyridine.

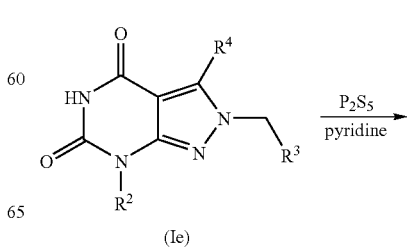

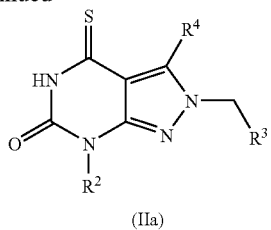

(IIa)

Compounds of formula II (A is N) may by formed by reacting compounds of formula IIa with an appropriate acylhydrazide, mercury chloride in acetonitrile with heat as set forth below:

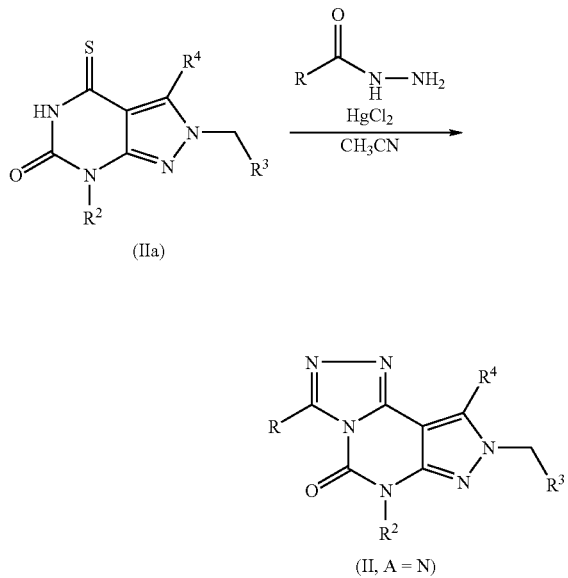

Compounds of formula II (A is CH) may also by formed by reacting compounds of formula IIa with an appropriate aminoketone, mercury chloride in acetonitrile with heat as set forth below:

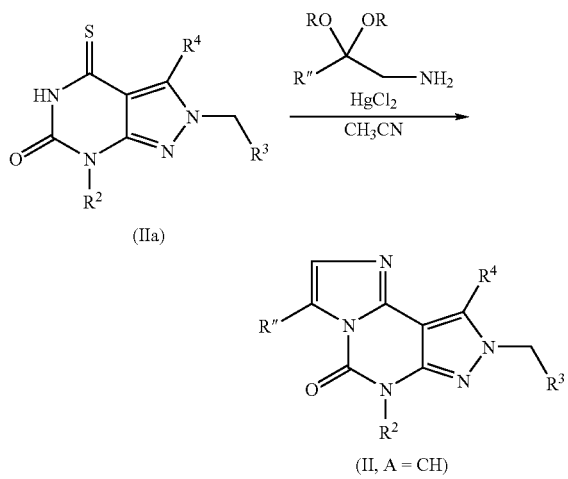

EXAMPLES

Chemical abbreviations used in the Examples are defined as follows: Boc denotes t-butoxycarbonyl, Cbz denotes benzyloxycarbonyl, DCM denotes methylene chloride, DIPEA denotes diisopropylethylamine, DMF denotes N,N-dimethylformamide, DMSO denotes dimethyl sulfoxide, $Et_2O$ denotes diethyl ether, EtOAc denotes ethyl acetate, TFA denotes trifluoroacetic acid, THF denotes tetrahydrofuran. Solvent mixture compositions are given as volume percentages or volume ratios. In cases where the NMR spectrum is complex, only diagnostic signals are reported.

Other terms used in the Examples are defined as follows: atm. denotes atmospheric pressure, equiv. denotes equivalent(s), h denotes hour(s), $T_b$ denotes bath temperature, HPLC denotes high performance liquid chromatography, min denotes minutes, NMR denotes nuclear magnetic resonance, psi denotes pounds per square inch.

(i) temperatures are given in degrees Celsius (° C.); unless otherwise stated, operations were carried out at room or ambient temperature, that is, at a temperature in the range of 18-25° C.;

(ii) organic solutions were dried over anhydrous magnesium sulfate or sodium sulfate; evaporation of solvent was carried out using a rotary evaporator under reduced pressure (600-4000 Pascals; 4.5-30 mm Hg) with a bath temperature of up to 60° C.;

(iii) chromatography means flash chromatography on silica gel or by FlashMaster™ II by Jones Chromatography using Isolute columns; thin layer chromatography (TLC) was carried out on silica gel plates;

(iv) in general, the course of reactions was followed by TLC or analytical HPLC and reaction times are given for illustration only;

(v) melting points are uncorrected and (dec) indicates decomposition;

(vi) final products had satisfactory proton nuclear magnetic resonance (NMR) spectra;

(vii) when given, NMR data is in the form of delta values for major diagnostic protons, given in parts per million (ppm) relative to tetramethylsilane (TMS) as an internal standard, determined at 300 or 500 MHz using deuterated chloroform ($CDCl_3$) or DMSO-$d_6$ or $CD_3OD$ as solvent; conventional abbreviations for signal shape are used; for AB spectra the directly observed shifts are reported; coupling constants (J) are given in Hz; Ar designates an aromatic proton when such an assignment is made;

(viii) reduced pressures are given as absolute pressures in pascals (Pa); elevated pressures are given as gauge pressures in bars;

(ix) solvent ratios are given in volume:volume (v/v) terms; and (x) Mass spectra (MS) were run using an automated system with atmospheric pressure electrospray ionization (ESI). Generally, only spectra where parent masses are observed are reported. The lowest mass major ion is reported for molecules where isotope splitting results in multiple mass spectral peaks (for example when chlorine is present).

The invention will now be illustrated by the following non-limiting examples.

Example 1

5-{8-[(6-chloroquinolin-4-yl)methyl]-6-isobutyl-5-oxo-2,5,6,8-tetrahydro-3H-imidazo [1,2-c]pyrazolo [4,3-e]pyrimidin-9-yl}-1-methyl-1H-pyrrole-3-carbonitrile

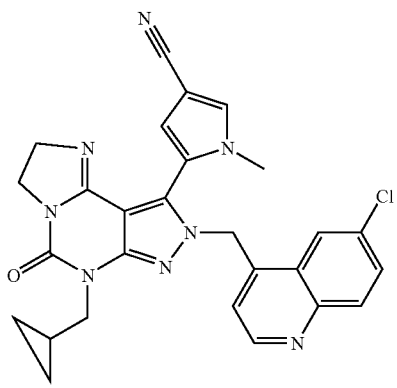

(a) 6-Chloro-1-cyclopropylmethylpyrimidine-2,4 [1H,3H]dione

6-Chlorouracil I (49.64 g, 0.34 mol; Lancaster) was dissolved in anhydrous DMSO (375 mL) and treated with solid $K_2CO_3$ (23.46 g, 0.17 mol) under nitrogen. The resulting white suspension was heated to ca. 80-90° C. and kept at this temperature for 2¼ h. Foaming was observed as the temperature increased, then the reaction mixture became mostly clear. Cyclopropylmethyl bromide (65 g, 0.48 mol) was added neat via syringe, resulting in a white fluffy precipitate. This was followed by a catalytic amount of KI (2.88 g, 0.017 mol). The reaction mixture was heated for 19 hr, becoming mostly homogenous, then turbid with white granular precipitate, and eventually orange as the reaction progressed, remaining heterogeneous. 375 mL 1 N NaOH (aq) was added to the hot reaction mixture, causing it to darken and clear. The heat was removed and the reaction mixture allowed to cool to room temperature while stirring. It was washed with 4×125 mL toluene and the organic washings discarded. The aqueous phase was brought to pH 2-3 by the addition of ca. 100 mL conc. HCl (aq.). 50 mL water was added, and precipitation began after about one hour at room temperature; cooling in ice completed the crystallization. The yellow-green solid was collected by filtration and washed with very cold ether to remove most of the color, then dried under vacuum. Yield: 29.37 g (43%) of a light yellow solid.

(b) 1-cyclopropylmethyl-6-hydrazinopyrimidine-2,4 [1H,3H]dione

6-Chloro-1-cyclopropylmethyluracil (24.34 g, 0.12 mol) was suspended in absolute ethanol (245 mL) under nitrogen. Anhydrous hydrazine (11.69 g, 0.36 mol) was added via syringe in excess, resulting in a clear-yellow solution. The reaction mixture was heated at 80-85° C. for one hour; bright yellow crystals began forming within minutes of the application of heat. The reaction mixture was cooled to room temperature and then in an ice bath, and the crude product collected by filtration. $N_2H_4 \times HCl$ was removed by triturating with cold water to give the product as a pale yellow solid, 20.47 g (86%). Mp 221° C. (dec).

(c) 6-chloroquinoline-4-carbaldehyde [3-(cyclopropylmethyl)-2,6-dioxo-1,2,3,6-tetrahydropyrimidin-4yl]hydrazone To a suspension of 1-cyclopropylmethyl-6-hydrazinopyrimidine-2,4[1H,3H]dione (5.05 g) in methanol (75 mL) was added 6-chloroquinoline 4-carbaldehyde (5.30 g). After stirring overnight, the reaction was filtered, yielding a yellow solid (10 g).

(d) 5-[2-[(6-chloroquinolin-4-yl)methyl]-7-(cycopropylmethyl)-4,6-dioxo4,5,6,7-tetrahydro -2H-pyrazolo[3,4-d]pyrimidin-3-yl]-1-methyl-1H-pyrrole-3-carbonitrile To a solution of 5-formyl-1-methyl-1H-pyrrole-3-carbonitrile (2.5 g) in DMF (50 mL) were added 6-chloroquinoline-4-carbaldehyde [3-(cyclopropylmethyl)-2,6-ioxo-1,2,3,6-tetrahydropyrimidin-4-yl]hydrazone (5.66 g) and piperdine (2 mL). After stirring overnight at $T_b=75°$ C., the reaction was diluted with ethyl acetate and water. The organic solution was collected, washed with saturated $NaHCO_3$ and brine, dried ($Na_2SO_4$), filtered and concentrated. The residue was purified by FlashMaster™ yielding 8.63 g of white solid. Mass: 486 $(M+H)^+$.

(e) 5-{2-[(6-chloroquinolin-4-yl)methyl]-7-(cyclopropylmethyl)-4-[(2-hydroxyethyl)amino]-6-oxo-6,7-dihydro-2H-pyrazolo[3,4-d]pyrimidin-3-yl}-1-methyl-1H-pyrrole-3-carbonitrile To a solution of 5-{2-[(6-chloroquinolin-4-yl)methyl]-7-cyclopropylmethyl-4,6-dioxo-4,5,6,7-tetrahydro-2H-pyrazolo[3,4-d]pyrimidin-3-yl}-1-methyl-1H-pyrrole-3-carbonitrile (0.42 g) in pyridine (5 mL) were added 4-chlorophenyl phosphorodichloridate (0.5 mL) and 3-nitro-1,2,4 triazole (0.15 g). After heating ($T_b=50°$ C.) for 3 h, the reaction was diluted with ethyl acetate. The organic solution was washed with saturated $NaHCO_3$ and brine, dried ($Na_2SO_4$), filtered and concentrated. The residue was dissolved in THF (10 mL) and ethanolamine (1.0 mL). After 3 h, the reaction was concentrated. This residue was purified by flash chromatography using a FlashMaster™ yielding 0.22 g, ES $(M+H)^+=529$.

(5) 5-[8-[(6-chloroquinolin-4-yl)methyl]-6-(cyclopropylmethyl)-5-oxo-2,5,6,8-tetrahydro-3H-imidazo [1,2-c]pyrazolo[4,3-e]pyrimidin-9-yl]-1-methyl-1H-pyrrole-3-carbonitrile To a solution of 5-{2-[(6-chloroquinolin-4-yl)methyl]-7-(cyclopropylmethyl)-4-[(2-hydroxyethyl)amino]-6-oxo-6,7-dihydro-2H-pyrazolo[3,4-a]pyrimidin-3-yl}-1-methyl-1H-pyrrole-3-carbonitrile (0.20 g) in $CH_2Cl_2$ (5 mL) were added triethylamine (0.30 mL) and methanesulfonlyl chloride (0.15 mL). After 30 min, the reaction was concentrated and purified by reverse phase HPLC with a Gilson system (54 mg). 1H NMR (300 MHz, CHLOROFORM-D) d ppm 0.50 (m, 4H) 1.39 (m, 1H) 3.32 (s, 3H) 3.93 (m, 6H) 5.70 (q, J=15.82 Hz, 2H) 6.59 (d, J=1.70 Hz, 1H) 6.78 (d, J=4.33 Hz, 1H) 7.26 (d, J=1.70 Hz, 1H) 7.71 (dd, J=9.04, 2.26 Hz, 1H) 7.88 (d, J=2.07 Hz, 1H) 8.11 (d, J=9.04 Hz, 1H) 8.82 (d, J=4.33 Hz, 1H); ES $(M+H)^+=512$.

Following the method of Example 1 and using the appropriate aldehydes and hydrazinopyrimidine-2,4[1H,3H]dione, Examples 2 to 7 were made by reaction of methanesulfonlyl chloride and the appropriate aminoalcohol precursor.

Example 2

5-{8-[(6-chloroquinolin-4-yl)methyl]-6-isobutyl-5-oxo-2,5,6,8-tetrahydro-3H-imidazo[1,2-c]pyrazolo[4,3-e]pyrimidin-9-yl}-1-methyl-1H-pyrrole-3-carbonitrile 1H NMR (300 MHz, CHLOROFORM-D) d ppm 0.98 (t, J=6.31 Hz, 6H) 1.28 (m, 3H) 2.34 (m, 1H) 3.29 (s, 2H) 3.82 (d, J=7.54 Hz, 1H) 3.94 (m, 4H) 5.69 (m, 2H) 6.59 (d, J=1.70 Hz, 1H) 6.75 (d, J=4.33 Hz, 1H) 7.27 (d, J=1.70 Hz, 1H) 7.71 (dd, J=8.95, 2.17 Hz, 1H) 7.91 (d, J=2.07 Hz, 1H) 8.11 (d, J=9.04 Hz, 1H) 8.81 (d, J=4.52 Hz, 1H); ES (M+H)⁺514.

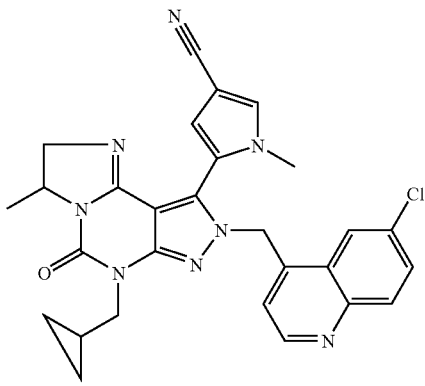

Example 4

5-[8-[(6-chloroquinolin-4-yl)methyl]-6-(cyclopropylmethyl)-2-methyl-5-oxo-2,5,6,8-tetrahydro-3H-imidazo[1,2-c]pyrazolo[4,3-e]pyrimidin-9-yl]-1-methyl-1H-pyrrole-3-carbonitrile 1H NMR (300 MHz, CHLOROFORM-D) d ppm 0.47 (m, 4H) 1.30 (m, 4H) 3.34 (d, J=18.84 Hz, 3H) 3.51 (s, 2H) 3.94 (m, 3H) 4.33 (m, 1H) 5.74 (m, 1H) 6.59 (s, 1H) 6.79 (d, J=4.33 Hz, 1H) 7.33 (m, 1H) 7.73 (s, 1H) 7.88 (s, 1H) 8.11 (d, J=9.04 Hz, 1H) 8.82 (d, J=4.52 Hz, 1H); ES (M+H)⁺525.

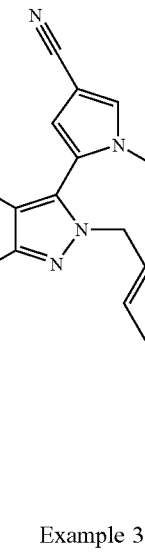

Example 3

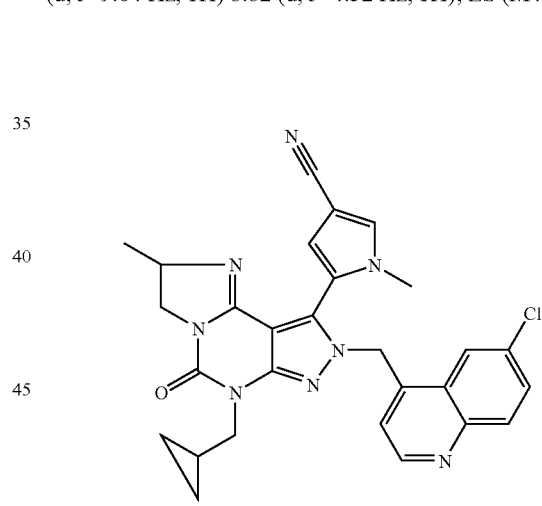

Example 5

Example 3

5-[8-[(6-chloroquinolin-4-yl)methyl]-6-(cyclopropylmethyl)-3-methyl-5-oxo-2,5,6,8-tetrahydro-3H-imidazo[1,2-c]pyrazolo[4,3-e]pyrimidin-9-yl]-1-methyl-1H-pyrrole-3-carbonitrile 1H NMR (300 MHz, CHLOROFORM-D) d ppm 0.50 (m, 4H) 1.41 (m, 4H) 3.33 (d, J=23.55 Hz, 3H) 3.57 (m, 1H) 3.87 (m, 2H) 4.11 (m, 1H) 4.43 (m, 1H) 5.70 (m, 2H) 6.59 (d, J=1.70 Hz, 1H) 6.79 (dd, J=8.57, 4.43 Hz, 1H) 7.28 (m, 1H) 7.71 (m, 1H) 7.89 (dd, J=8.38, 2.17 Hz, 1H) 8.11 (d, J=9.04 Hz, 1H) 8.82 (dd, J=4.33, 2.45 Hz, 1H); ES (M+H)⁺ 525.

Example 5

5-[(3R)-8-[(6-chloroquinolin-4-yl)methyl]-6-(cyclopropylmethyl)-3-methyl-5-oxo-2,5,6,8-tetrahydro-3H-imidazo[1,2-c]pyrazolo[4,3-e]pyrimidin-9-yl]-1-methyl-1H-pyrrole-3-carbonitrile 1H NMR (300 MHz, CHLOROFORM-D) d ppm 0.50 (m, 4H) 1.40 (m, 3H) 1.75 (m, 1H), 3.33 (d, J=23.36 Hz, 3H) 3.57 (m, 1H) 3.88 (m, 2H) 4.11 (m, 1H) 4.43 (m, 1H) 5.72 (m, 2H) 6.59 (d, J=1.70 Hz, 1H) 6.79 (dd, J=8.38, 4.43 Hz, 1H) 7.28 (m, 1H) 7.71 (m, 1H) 7.89 (dd, J=8.10, 2.07 Hz, 1H) 8.11 (d, J=9.04 Hz, 1H) 8.82 (dd, J=4.43, 2.35 Hz, 1H); ES (M+H)⁺525.

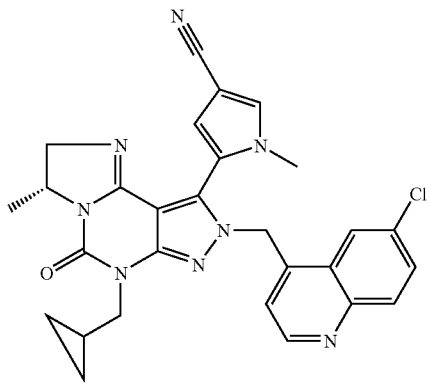

Example 6

5-[(3S)-8-[(6-chloroquinolin-4-yl)methyl]-6-(cyclopropylmethyl)-3-methyl-5-oxo-2,5,6,8-tetrahydro-3H-imidazo[1,2-c]pyrazolo[4,3-e]pyrimidin-9-yl]-1-methyl-1H-pyrrole-3-carbonitrile 1H NMR (300 MHz, CHLOROFORM-D) d ppm 0.50 (m, 4H) 1.41 (m, 3H) 1.77 (m, 1H) 3.32 (d, 3H) 3.56 (m, 1H) 3.88 (m, 1H) 4.10 (m, 1H) 4.41 (m, 1H) 5.71 (m, 2H) 6.59 (d, J=1.51 Hz, 1H) 6.79 (dd, J=8.29, 4.52 Hz, 1H) 7.28 (m, 1H) 7.71 (m, 1H) 7.89 (dd, J=8.10, 2.07 Hz, 1H) 8.11 (d, J=9.23 Hz, 1H) 8.82 (dd, J=4.33, 2.45 Hz, 1H); ES (M+H)+ 525.

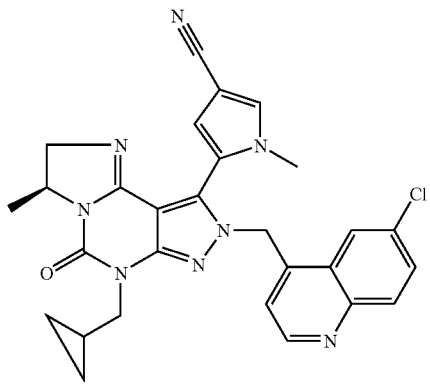

Example 7

5-[9-[(6-chloroquinolin-4-yl)methyl]-7-(cyclopropylmethyl)-6-oxo-2,3,4,6,7,9-hexahydropyrazolo[4,3-e]pyrimido[1,2-c]pyrimidin-10-yl]-1-methyl-1H-pyrrole-3-carbonitrile 1H NMR (300 MHz, DMSO-D6) d ppm 0.38 (m, 2H) 1.31 (m, 1H) 1.78 (m, 1H) 3.13 (s, 3 H) 3.30 (m, 2H) 3.77 (m, 2H) 5.82 (m, J=16.20 Hz, 1H) 6.72 (s, 1H) 6.77 (m, 1H) 7.67 (s, 1H) 7.80 (d, J=9.23 Hz, 1H) 8.05 (d, J=9.04 Hz, 1H) 8.11 (d, J=1.70 Hz, 1H) 8.80 (d, J=4.52 Hz, 1H); ES (M+H)+525.

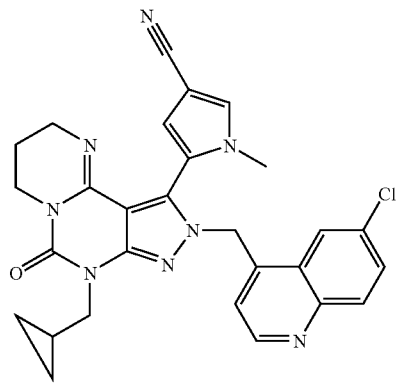

Example 8

5-[8-[(6-chloroquinolin-4-yl)methyl]-6-(cyclopropylmethyl)-5-oxo-6,8-dihydro-5H-pyrazolo[4,3-e][1,2,4]triazolo[4,3-c]pyrimidin-9-yl]-1-methyl-1H-pyrrole-3-carbonitrile

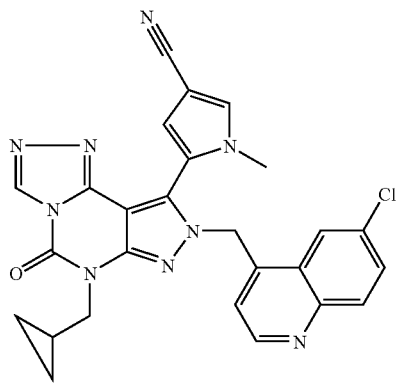

(a) 5-[2-[(6-chloroquinolin-4-yl)methyl]-7-(cyclopropylmethyl)-6-oxo-4-thioxo-4,5,6,7-tetrahydro-2H-pyrazolo[3,4-d]pyrimidin-3-yl]-1-methyl-1H-pyrrole-3-carbonitrile To a solution of 5-[2-[(6-chloroquinolin-4-yl)methyl]-7-(cyclopropylmethyl)-4,6-dioxo-4,5,6,7-tetrahydro-2H-pyrazolo[3,4-d]pyrimidin-3yl]-1methyl-1H-pyrrole-3-carbonitrile (0.53 g) in pyridine (5 mL) was added $P_4S_{10}$ (0.52 g). The mixture was heated by microwave at 140° C. for 100 minutes. The mixture was diluted with water and ethyl acetate. The organic solution was collected, washed with saturated $NaHCO_3$ and brine, dried ($Na_2SO_4$), filtered and concentrated. The residue was purified by flash chromatography using a FlashMaster™ yielding 0.44 g.

(b) 5-[8-[(6-chloroquinolin-4-yl)methyl]-6-(cyclopropylmethyl)-5-oxo-6,8-dihydro-5H-pyrazolo[4,3-e][1,2,4]triazolo[4,3-c]pyrimidin-9-yl]-1-methyl-1H-pyrrole-3-carbonitrile To a solution of 5-[2-[(6-chloroquinolinyl)methyl]-7-(cyclopropylmethyl)-6-oxo-4-thioxo-4,5,6,7-tetrahydro-2H- pyrazolo[3,4-d]pyrimidin-3-yl]-1-methyl- 1H-pyrrole-3-carbonitrile (0.14 g) in acetonitrile (5 mL) and formic hydrazide (80 mg) was added mercury(II) chloride (160 mg). After stirring overnight at rt, the reaction was warmed ($T_b$=70 C). After 5 h with heat, the reaction was filtered through a celite bed and concentrated. The residue was purified by flash chromatography using a FlashMaster™ yielding 44 mg, 1H NMR (300 MHz, CHLOROFORM-D) d ppm 0.57 (m, 4H) 1.48 (m, J=10.93 Hz, 1H) 3.45 (s, 3H) 4.15 (t, J=6.59 Hz, 2H) 5.86 (m, 2H) 6.68 (d, J=1.70 Hz, 1H) 6.83 (d, J=4.52 Hz, 1H) 7.40 (d, J=1.70 Hz, 1H) 7.72 (dd, J=8.95, 2.17 Hz, 1H) 7.88 (d, J=2.07 Hz, 1H) 8.13 (d, J=8.85 Hz, 1H) 8.84 (d, J=4.33 Hz, 1H) 8.93 (s, 1H);
ES M+H$^+$=510.

Example 9

5-[8-[(6-chloroquinolin-4-yl)methyl]-6-(cyclopropylmethyl)-3-methyl-5-oxo-6,8-dihydro-5H-pyrazolo[4,3-e][1,2,4]triazolo[4,3-]pyrimidin-9-yl]-1-methyl-1H-pyrrole-3-carbonitrile

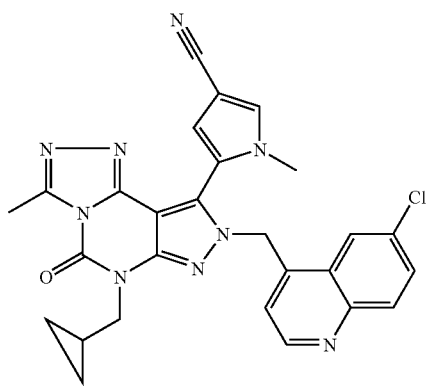

To a suspension of 5-[2-[(6-chloroquinolin-4-yl)methyl]-7-(cyclopropylmethyl)-6-oxo-4-thioxo-4,5,6,7-tetrahydro-2H-pyrazolo[3,4-d]pyrimidin-3-yl]-1-methyl-1H-pyrrole-3-carbonitrile (0.12 g) in acetonitrile (3 mL) were added acetic hydrazide (50 mg) and mercury chloride (0.13 g). The reaction was stirred at rt for 1 h and then heated by microwave at 100° C. for 30 min. The reaction was concentrated, redissolved in ethyl acetate and water, and filtered through a celite bed. The organic solution was collected, washed with brine, dried (Na$_2$SO$_4$), filtered and concentrated. The residue was purified by flash chromatography using a FlashMaster™ yielding 119 mg of a white foam, 1H NMR (300 MHz, CHLOROFORM-D) d ppm 0.56 (m, 4H) 1.47 (s, 1H) 2.90 (s, 3H) 3.43 (s, 3H) 4.09 (m, 2H) 5.86 (m, 2H) 6.65 (d, J=1.70 Hz, 1H) 6.81 (d, J=4.52 Hz, 1H) 7.38 (d, J=1.51 Hz, 1H) 7.72 (dd, J=8.95, 2.17 Hz, 1H) 7.88 (d, J=2.07 Hz, 1H) 8.12 (d, J=9.04 Hz, 1H) 8.83 (d, J=4.33 Hz, 1H); ES M+H$^+$=523.

Example 10

5-[8-[(6-chloroquinolin-4-yl)methyl]-6-cyclopropylmethyl)-3-(dimethylamino)-5-oxo-6,8-dihydro-5H-pyrazolo[4,3-e][1,2,4]triazolo[4,3-c]pyrimidin-9-yl]-1-methyl-1H-pyrrole-3-carbonitrile

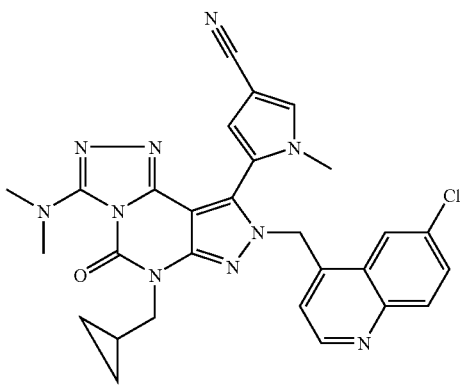

(a) 5-[2-[(6-chloroquinolin-4-yl)methyl]-7-(cyclopropylmethyl)-4-hydrazino-6-oxo-6,7-dihydro-2H-pyrazolo[3,4-d]pyrimidin-3-yl]-1-methyl-1H-pyrrole-3-carbonitrile To a solution of 5-[2-[(6-chloroquinolin-4-yl)methyl]-7-(cyclopropylmethyl)-6-oxo-4-thioxo-4,5,6,7-tetrahydro-2H-pyrazolo[3,4-d]pyrimidin-3-yl]-1-methyl-1H-pyrrole-3-carbonitrile (0.24 g) in THF (5 mL) were added hydrazine hydrate (0.30 mL) and mercury chloride (0.30 g). After 4 h, a second addition of hydrazine hydrate (0.20 mL) and mercury chloride (0.30 g) was done. After stirring overnight, the mixture was diluted with water and ethyl acetate. The mixture was then filtered through a celite bed. The organic solution was collected, washed with saturated NaHCO$_3$ and brine, dried (Na$_2$SO$_4$), filtered and concentrated. The residue was purified by flash chromatography using a FlashMaster™ yielding 0.18 g.

(b) 5-[8-[(6-chloroquinolin-4-yl)methyl]-6-(cyclopropylmethyl)-3-(dimethylamino)-5-oxo-6,8-dihydro-5H-pyrazolo[4,3-e][1,2,4]triazolo[4,3-c]pyrimidin-9-yl]-1-methyl-1H-pyrrole-3-carbonitrile To a solution of 5-[2-[(6-chloroquinolin-4-yl)methyl]-7-(cyclopropylmethyl)-4-hydrazino-6-oxo-6,7-dihydro-2H-pyrazolo[3,4d]pyrimidin-3-yl]-1-methyl-1H-pyrrole-3-carbonitrile (0.13 g) in dioxane (3 mL) was added phosgene iminium chloride (0.12 g). The reaction was heated by microwave at 100° C. for 5 min. The mixture was concentrated and purified by RP-HPLC yielding 94 mg of yellow foam, 1H NMR (300 MHz, CHLOROFORM-D) d ppm 0.56 (m, 4H) 1.44 (m, J=7.35 Hz, 1H) 3.06 (s, 6H) 3.46 (s, 3H) 4.10 (m, 2H) 5.84 (m, 2H) 6.62 (d, J=1.70 Hz, 1H) 6.81 (d, J=4.52 Hz, 1H) 7.35 (d, J=1.70 Hz, 1H) 7.71 (dd, J=9.04, 2.07 Hz, 1H) 7.87 (d, J=2.07 Hz, 1H) 8.12 (d, J=9.04 Hz, 1H) 8.83 (d, J=4.52 Hz, 1H); ES M+H$^+$=553.

Example 11

5-[3-amino-8-[(6-chloroquinolin-4-yl)methyl]-6-(cyclopropylmethyl)-5-oxo-6,8-dihydro-5H-pyrazolo[4,3-e][1,2,4]triazolo[4,3-c]pyrimidin-9-yl]-1-methyl-1H-pyrrole-3-carbonitrile

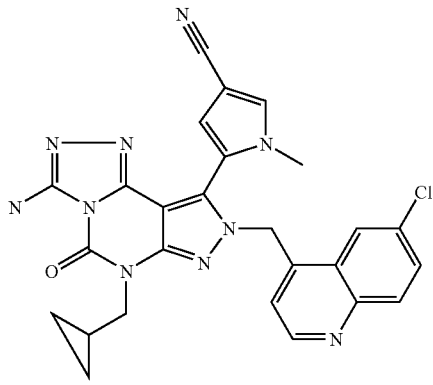

To a solution of 5-[2-[(6-chloroquinolin-4-yl)methyl]-7-(cyclopropylmethyl)-4-hydrazino-6-oxo-6,7-dihydro-2H-pyrazolo[3,4-d]pyrimidin-3-yl]-1-methyl-1H-pyrrole-3-carbonitrile (0.13 g) in dioxane (3 mL) was added cyanogen bromide (0.15 mL). The reaction was heated by microwave at 100° C. for 5 min. The mixture was concentrated and purified by HPLC yielding 27 mg of yellow foam, 1H NMR (300 MHz, CHLOROFORM-D) d ppm 0.56 (m, 4 H) 1.44 (m, 1H) 3.7 (s, 3H) 3.94 (m, 2H) 5.84 (m, 2H) 6.54 (d, 1H) 6.86 (m, 1H) 7.71 (m, 2H) 7.87 (m, 1H) 8.12 (m, 1H) 8.85 (m, 1H); ES M+H$^+$=525.

Example 12

5-[8-[(6-chloroquinolin-4-yl)methyl]-6-(cyclopropylmethyl)-5-oxo-6,8-dihydro-5H-imidazo[1,2-c]pyrazolo[4,3-e]pyrimidin-9-yl]-1-methyl-1H-pyrrole-3-carbonitrile

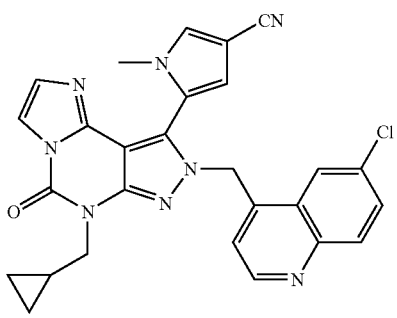

5-[2-[(6-chloroquinolin-4-yl)methyl]-7-(cyclopropylmethyl)-6-oxo-4-thioxo-4,5,6,7-tetrahydro-2H-pyrazolo[3,4-d]pyrimidin-3-yl]-1-methyl-1H-pyrrole-3-carbonitrile (130 mg, 0.26 mmol) was dissolved in 5 mL of anhydrous acetonitrile. 2-Aminoacetaldehyde dimethyl acetal (55 mg, 0.52 mmol, 2.0 eq.) was added and the solution stirred 5 minutes. Mercury(II) chloride (176 mg, 0.65 mmol, 2.5 eq.) was added and the mixture heated in the microwave reactor at 130° C. for 70 minutes. The resulting dark solution was diluted in 30 mL water and 30 mL dichloromethane and filtered through celite to remove the dark precipitate. The celite pad was washed repeatedly with small amounts of dichloromethane. The organic layer was dried over sodium sulfate, filtered and concentrated on the rotary evaporator. The crude product was purified by chromatography on silica (gradient: hexane to ethyl acetate). The resulting product was still impure so it was re-purified by chromatography on silica (gradient: dichloromethane to 10% methanol in dichloromethane). The product was then recrystallized by dissolving in a minimum of dichloromethane (ca. 0.5 mL) followed by addition of six volumes of methanol. Isolated 91 mg (68% yield) of the product as small yellow crystals. 1H NMR (300 MHz, CHLOROFORM-D) d ppm 0.55 (m, 4H) 1.48 (m, 1H) 3.36 (s, 3H) 4.15 (m, 2H) 5.81 (m, 2H) 6.64 (d, J=1.70 Hz, 1H) 6.76 (d, J=4.33 Hz, 1H) 7.22 (d, J=1.51 Hz, 1H) 7.35 (d, J=1.51 Hz, 1H) 7.69 (m, 2H) 7.91 (d, J=2.07 Hz, 1H) 8.08 (d, J=9.04 Hz, 1H) 8.80 (d, J=4.52 Hz, 1H); ES M+H$^+$=510.

Following the method of Example 12 and preparing the appropriate amide following Example 1, the following examples were made from 1-cyclopropylmethyl-6-hydrazinopyrimidine-2,4[1H,3H]dione.

Example 13

8-[(6-chloroquinolin-4-yl)methyl]-6-(cyclopropylmethyl)-9-(1-methyl-1H-imidazol-5-yl)-6,8-dihydro-5H-imidazo[1,2-c]pyrazolo[4,3-e]pyrimidin-5-one aldehydes: 1(c) 6-chloroquinoline 4-carbaldehyde; 1(d) 1-methyl-1H-imidazole-5-carbaldehyde 1H NMR (300 MHz, CHLOROFORM-D) d ppm 0.55 (s, 4H) 1.51 (s, 1H) 3.51 (s, 3H) 4.18 (m, 2H) 5.82 (m, 2H) 6.77 (d, J=4.33 Hz, 1H) 7.22 (d, 1H) 7.26 (d, 1H) 7.70 (m, 2H) 7.76 (d, J=1.51 Hz, 1H) 7.94 (d, J=2.07 Hz, 1H) 8.11 (d, J=9.04 Hz, 1H) 8.81 (d, J=4.52 Hz, 1 H); ES (M+H)$^+$485

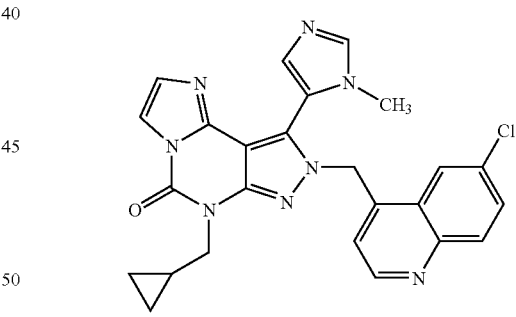

Example 14

8-{[5-chloro-1-(methylsulfonyl)-1H-indol-3-yl]methyl}-6-(cyclopropylmethyl)-9-(1-methyl-1H-imidazol-5-yl)-6,8-dihydro-5H-imidazo[1,2-c]pyrazolo[4,3-e]pyrimidin-5-one aldehydes: 1(c) 5-chloro-1-(methylsulfonyl)-1H-indole-3-carbaldehyde; 1(d) 1-methyl-1H-imidazole-5-carbaldehyde 1H NMR (300 MHz, CHLOROFORM-D) d ppm 0.60 (m, 4H) 1.52 (m, 1H) 3.13 (s, 3H) 3.51 (s, 3H) 4.19 (d, J=7.16 Hz, 2H) 5.53 (m, J=48.79 Hz, 2H) 7.18 (s, 1H) 7.23 (d, J=1.51 Hz, 1H) 7.34 (m, 2H) 7.45 (d, J=1.51 Hz, 1 H) 7.75 (m, 3H); ES (M+H)$^+$552

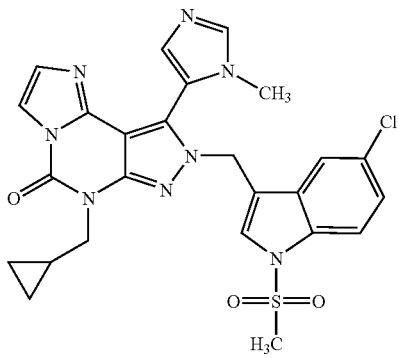

Example 15

8-[(6-chloroquinolin-4-yl)methyl]-6-(cyclopropylmethyl)-9-[1-methyl-4-(methylsulfonyl)-1H-pyrrol-2-yl]-6,8-dihydro-5H-imidazo[1,2-c]pyrazolo[4,3-e]pyrimidin-5-one aldehydes: 1(c) 6-chloroquinoline 4-carbaldehyde; 1(d) 1-methyl-4-(methylsulfonyl)-1H-pyrrole-2-carbaldehyde 1H NMR (300 MHz, DMSO-D6) d ppm 0.48 (s, 3H) 1.41 (s, 1H) 3.09 (s, 3H) 3.32 (m, 3H) 4.04 (s, 1H) 6.03 (m, 1H) 6.81 (d, J=1.51 Hz, 1H) 6.88 (d, J=4.71 Hz, 1H) 7.26 (d, J=1.32 Hz, 1H) 7.70 (d, J=1.51 Hz, 1H) 7.83 (m, 2H) 8.07 (d, J=9.04 Hz, 1H) 8.16 (s, 1H) 8.81 (d, J=4.52 Hz, 1H); ES (M+H)$^+$563

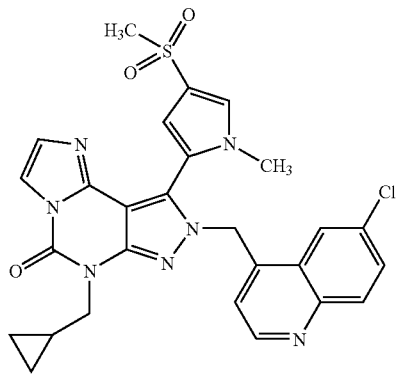

Example 16

5-[8-{[5-chloro-1-methylsulfonyl)-1H-indol-3-yl]methyl}-6-(cyclopropylmethyl)-5-oxo-6,8-dihydro-5H-imidazo[1,2-c]pyrazolo[4,3-e]pyrimidin-9-yl]-1-methyl-1H-pyrrole-3-carbonitrile aldehydes: 1(c) 5-chloro-1-(methylsulfonyl)-1H-indole-3-carbaldehyde; 1(d) 5-formyl-1-methyl-1H-pyrrole-3-carbonitrile 1H NMR (300 MHz, DMSO-D6) d ppm 0.52 (m, 4H) 1.41 (s, 1H) 3.30 (m, 4H) 3.46 (s, 3H) 4.05 (s, 2H) 5.61 (m, J=31.65 Hz, 2H) 7.05 (d, J=1.70 Hz, 1H) 7.22 (d, J=1.51 Hz, 1H) 7.32 (s, 1H) 7.41 (dd, J=8.85, 2.07 Hz, 1H) 7.55 (d, J=2.07 Hz, 1H) 7.80 (m, 2H) 7.94 (d, J=1.51 Hz, 1H); ES (M+H)$^+$576

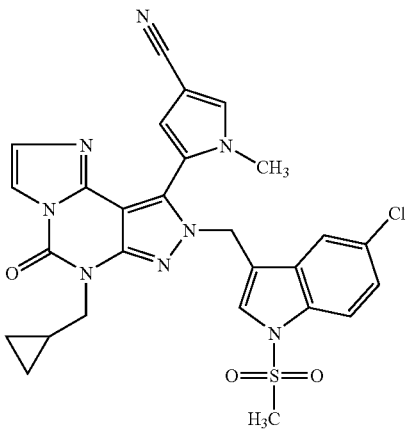

Example 17

5-[8-[(6-chloroquinolin-4-yl)methyl]-6-(cyclopropylmethyl)-3-methyl-5-oxo-6,8-dihydro-5H-imidazo[1,2-c]pyrazolo[4,3-e]pyrimidin-9-yl]-1-methyl-1H-pyrrole-3-carbonitrile

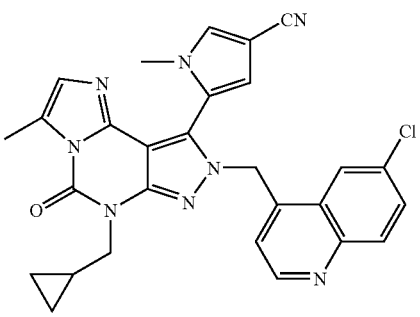

a) 5-[4-amino-2-[(6-chloroquinolin-4-yl)methyl]-7-(cyclopropylmethyl)-6-oxo-6,7-dihydro-2H-pyrazolo[3,4-d]pyrimidin-3-yl]-1-methyl-1H-pyrrole-3-carbonitrile

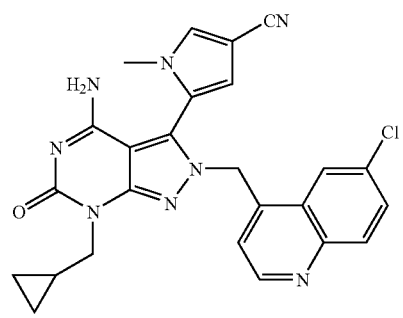

5-[2-[(6-chloroquinolin-4-yl)methyl]-7-(cyclopropylmethyl)-6-oxo-4-thioxo-4,5,6,7-tetrahydro-2H-pyrazolo[3,4-d]pyrimidin-3-yl]-1-methyl-1H-pyrrole-3-carbonitrile (0.5g, 1.0 mmol) was dissolved in 10 mL anhydrous THF. Anhydrous ammonia in methanol (20 mL of 2M solution) was added, followed by mercury (II) chloride (410 mg, 1.5 mmol, 1.5 eq). The mixture was heated to 60° C. for 48 h. Volatiles were evaporated and the residue dissolved in 100 mL ethyl acetate, 50 mL dichloromethane, and 100 mL water. The organic layer was washed with water (100 mL) and dried over sodium sulfate. The residue was purified by chromatography on silica (gradient: dichloromethane to 10% methanol in dichloromethane), yielding 232 mg (48%) of the product as a yellow solid. ES M+H+=485.

b) 5-[8-[(6-chloroquinolin-4-yl)methyl]-6-(cyclopropylmethyl)-3-methyl-5-oxo-6,8-dihydro-5H-imidazo[1,2-c]pyrazolo[4,3-e]pyrimidin-9-yl]-1-methyl-1H-pyrrole-3-carbonitrile 5-[4-amino-2-[(6-chloroquinolin-4-yl)methyl]-7-(cyclopropylmethyl)-6-oxo-6,7-dihydro-2H-pyrazolo[3,4-d]pyrimidin-3-yl]-1-methyl-1H-pyrrole-3-carbonitrile (75 mg, 0.15 mmol) was dissolved in 1.5 mL anhydrous DMF with 30 mg DBU. Chloroacetone (28 mg, 0.3 mmol, 2.0 eq.) was added and the resulting solution heated in the microwave for 90 minutes at 125° C. Two addition eq. chloroacetone were added, and the reaction returned to the microwave and heated an additional 90 minutes at 125° C. The reaction mixture was diluted with 50 mL. water and 50 mL ethyl acetate. The aqueous layer was washed 3×50 mL with ethyl acetate. The combined organic fractions were washed with 50 mL brine and dried over sodium sulfate. The crude product was purified by chromatography on silica (gradient: dichloromethane to 10% methanol in dichloromethane), followed by reverse phase HPLC using 40% aqueous acetonitrile, yielding 20 mg product. 1H NMR (300 MHz, CHLOROFORM-D) d ppm 0.55 (m, 4H) 1.48 (m, 1H) 2.27 (d, J=0.94 Hz, 3H) 3.42 (s, 3 H) 4.13 (m, 2H) 5.82 (m, 2H) 6.62 (dd, J=4.52, 1.88 Hz, 1H) 6.76 (d, J=4.33 Hz, 1H) 7.36 (d, J=1.51 Hz, 1H) 7.44 (d, J=1.13 Hz, 1H) 7.70 (dd, J=9.04, 2.26 Hz, 1H) 7.90 (d, J=2.26 Hz, 1H) 8.10 (m, 1H) 8.81 (d, J=4.52 Hz, 1H); ES M+H+=524.

The compounds of the present invention have utility for the prevention and treatment of *H. pylori* infection. Methods of treatment target the prevention of cell wall biosynthesis through the MurI enzyme. Compounds that inhibit MurI activity control the production of cell wall biosynthesis. The inhibition of MurI will inhibit growth of *H. pylori* and will reduce or prevent the diseases resulting from *H. pylori* infection such as peptic ulcers, gastritis and MALT lymphoma The compounds of the present invention have utility for the prevention and treatment of such disorders.

Compounds of the present invention have been shown to inhibit MurI, as determined by glutamate racemase activity assay described herein. Compounds provided by this invention should also be useful as standards and reagents in determining the ability of a potential pharmaceutical to inhibit MurI. These would be provided in commercial kits comprising a compound of this invention.

As used herein "rt" denotes room temperature, "ug" denotes microgram, "mg" denotes milligram, "g" denotes gram, "uL" denotes microliter, "mL" denotes milliliter, "L" denotes liter, "nM" denotes nanomolar, "uM" denotes micromolar, "mM" denotes millimolar, "M" denotes molar, "nm" denotes nanometer, "DMSO" denotes dimethyl sulfoxide, "DTT" denotes dithiothreitol, "EDTA" denotes ethylenediaminetetraacetate, Glutamate Racemase Activity Assay:

Glutamate racemase (MurI) activity was assayed by measuring the conversion of glutamate from the D to the L enantiomer. This reaction was coupled to the reduction of NAD+ to NADH by L-glutamate dehydrogenase (LGDH). LGDH from bovine liver was obtained as a lyophilized powder (Roche #197734) and dissolved in buffer containing 10 mM Tris (Sigma #T-6791), pH 7.5, 0.1 mM EDTA (Fisher #BP118-500) and 50% (weight/volume) glycerol (Sigma #G-9012). The assay mixture consisted of 100 mM Tris-HCl, pH 8.0, 10 mM β-NAD (Sigma #N-1511), 5 mM DTT (Sigma #D-5545), 0.03% PEG (mw 8000, Sigma #P-5413), 0.03 mg/mL BSA (Pierce #23210), 15 U/mL LGDH, D-glutamate (40 μM, Fluka #49460), and purified MurI (50 nM or 1 uM). The assay was performed in 96-well black microtiter plates (Greiner #XN2-9511) in a final assay volume of 100 μL. Compounds were prepared as 20 mM stock solutions in dimethyl sulfoxide (DMSO, Sigma #D-5879) and serial dilutions were prepared from these solutions using DMSO, 2 μL of which were added to the wells. Activity at room temperature was measured by monitoring the increase in fluorescence using a TECAN Ultra plate reader with 340 nm excitation and 465 nm emission filters. The compounds described have a measured IC$_{50}$ in this assay of less than 400 μM.

The invention claimed is:
1. A compound having the structural formula (I):

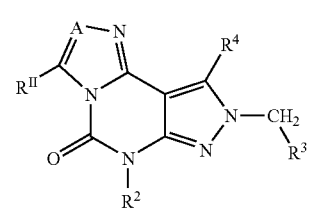

wherein,
A is N or CR$^I$;
R$^I$ is, independently at each instance, H, halogen, cyano, nitro, alkyl, alkenyl, alkynyl, alkoxy, amino, carboxy, alkylcarbonyl, alkylcarbamide, alkylsulfide, alkylsulphone, alkylsulfoxide, sulphamide;
R$^{II}$ is, independently at each instance, H, halogen, cyano, nitro, alkyl, alkenyl, alkynyl, alkoxy, amino, carboxy, alkylcarbonyl, alkylcarbamide, alkylsulfide, alkylsulphone, sulfoxide, sulphamide;
R$^2$ is H, alkyl, wherein said alkyl is optionally substituted with 0, 1, 2 or 3 substituents selected from heterocycle, S(=O)$_n$R$^C$, —S(=O)$_n$NR$^a$R$^a$ halogen, —CN, —OR$^a$, —NR$^a$R$^a$, —C(=O)OR$^a$, —C(=O)R$^a$, —C(=O) NR$^a$R$^a$, —OC(=O)C$_{1-4}$alkyl, or —NR$^a$C(=O)C$_{1-4}$ alkyl, alkylcycloalkyl, wherein said alkylcycloalkyl is optionally substituted with 0, 1, 2 or 3 substituents selected from heterocycle, S(=O)$_n$R$^c$, —S(=O)$_n$ NR$^a$R$^a$ halogen, —CN, OR$^a$, —NR$^a$R$^a$, —C(=O)OR$^a$, —C(=O)R$^a$, —C(=O)NR$^a$R$^a$, —OC(=O)C$_{1-4}$alkyl, or —NR$^a$C(=O)C$_{1-4}$alkyl, alkenyl, alkynyl, cycloalkyl, cycloalkenyl, cycloalkynyl, aryl, alkoxy, amino, or heterocycle;
R$^3$ is a monocyclic or bicyclic, saturated or unsaturated, ring system comprising 0, 1, 2 or 3 heteroatoms independently selected from N, O, or S, the ring being substituted by 0, 1, 2 or 3 substituents selected from =O, halogen, —OR$^a$, C$_{1-6}$-alkyl, C$_{1-6}$haloalkyl, —CN, nitro, —S(=O)$_n$R$^c$, —O(CH$_2$)$_m$Het, —O(CH$_2$)$_m$C(=O)Het, —O(CH$_2$)$_m$C(=O)NR$^a$R$^a$, —O(CH$_2$)$_m$C(=O)OR$^a$, —O(CH$_2$)$_m$NR$^a$R$^a$, —O(CH$_2$)$_m$OR$^a$, —S(CH$_2$)$_m$Het, —S(CH$_2$)$_m$C(=O)Het, —S(CH$_2$)$_m$C(=O)NR$^a$R$^a$, —S(CH$_2$)$_m$C(=O)OR$^a$, —S(CH$_2$)$_m$NR$^a$R$^a$, —S(CH$_2$)$_m$OR$^a$, —NR$^a$R$^a$, —NHC(=O)R$^a$, N=NR$^a$, aminocarbonyl, phenyl, benzyl; or R$^3$ is represented by -Het, -Het-Het, R$^5$, —R$^5$-Het, -Het-R$^5$, -Het-O—R$^5$, —R$^5$—R$^5$, —R$^5$—OR$^5$;

R$^4$ is a monocyclic or bicyclic, saturated or unsaturated, ring system, or a vicinal-fused derivative thereof, which may contain from 5 to 12 ring atoms, 0, 1, 2, 3 or 4 of which are heteroatoms independently selected from N, O, or S, the ring system being substituted by 0, 1, 2 or 3 substituents selected from B(OH)$_2$, vicinal —OCH$_2$CH$_2$O—, vicinal —OC$_{1-2}$haloalkylO—, vicinal —OCH$_2$O—, vicinal —CH$_2$OCH$_2$O—, =O, halogen, —R$^b$OR$^a$, —SR$^a$, —OR$^a$, C$_{1-6}$alkyl, C$_{1-6}$haloalkyl, —CN, —S(=O)$_n$R$^c$, —O(CH$_2$)$_m$Het, —O(CH$_2$)$_m$C(=O)Het, —O(CH$_2$)$_m$C(=O)NR$^a$R$^a$, —O(CH$_2$)$_m$C(=O)OR$^a$, —O(CH$_2$)$_m$NR$^a$R$^a$, —O(CH$_2$)$_m$OR$^a$, —S(CH$_2$)$_m$Het, —S(CH$_2$)$_m$C(=O)Het, —S(CH$_2$)$_m$C(=O)NR$^a$R$^a$, —S(CH$_2$)$_m$C(=O)OR$^a$, —S(CH$_2$)$_m$NR$^a$R$^a$, —S(CH$_2$)$_m$OR$^a$, —NR$^a$R$^a$, —NHC(=O)R$^a$, —NHC(=O)OR$^a$, N=NR$^a$, NO$_2$, —C(=O)NR$^a$R$^a$, —C(=O)NR$^a$OR$^a$, —C(=O)NR$^a$(R$^b$NR$^a$R$^a$), —C(=O)NR$^a$(R$^b$OR$^a$), —C(=O) NR$^a$(R$^b$S(=O)R$^a$), —C(=O)NR$^a$(R$^b$Het), —C(=O)OR$^a$, —OC(=O)R$^a$, —C(=O)OR$^b$NR$^a$R$^a$, —C(=O)R$^a$, —C(=O)R$^b$NR$^a$R$^a$, —C(=NOR$^a$)R$^a$, —C(=NCN) R$^a$, —S(=O)$_2$NR$^a$R$^a$, —NR$^a$S(=O)$_2$R$^a$, —S(=O)$_2$NR$^a$(R$^b$C(=O)NR$^a$R$^a$), —S(=O)$_2$NR$^a$(R$^b$C(=O)OR$^a$), aminocarbonyl, phenyl, benzyl; or R$^4$ is represented by —(CH$_2$)$_n$R$^5$-Het, —(CH$_2$)$_n$R$^d$, -Het, -Het-Het, R$^5$, —R$^5$-Het, -Het-R$^5$, -Het-OR$^5$, R$^5$—R$^5$, or —R$^5$—OR$^5$; or R$^4$ is represented by C$_{1-6}$alkyl, —NC$_{1-6}$ alkyl, or —N(C$_{1-6}$alkyl)$_2$ wherein the C$_{1-6}$alkyl, —NC$_{1-6}$alkyl, —N(C$_{1-6}$alkyl) are substituted by 0, 1 or 2 substituents selected from R$^a$, OR$^a$, halogen or phenyl wherein R$^4$ is not —(CH$_2$)$_z$CH$_3$, —(CH$_2$)$_z$CH$_2$OH, —(CH$_2$)$_z$CO$_2$H, or —(CH$_2$)$_z$CO$_2$C$_{1-6}$alkyl wherein z is 1,2,3,4,5, or 6;

R$^5$ is independently at each instance, phenyl substituted by 0, 1, 2, or 3 groups selected from halogen, C$_{1-6}$haloalkyl, —OC$_{1-6}$haloalkyl, C$_{1-6}$alkyl, —CN, nitro, —OR$^a$, —S(=O)$_n$R$^c$, —O(CH$_2$)$_m$Het, —O(CH$_2$)$_m$C(=O)Het, —O(CH$_2$)$_m$C(=O)NR$^a$R$^a$, —O(CH$_2$)$_m$C(=O)OR$^a$, —O(CH$_2$)$_m$NR$^a$R$^a$, —O(CH$_2$)$_m$OR$^a$, —S(CH$_2$)$_m$Het, —S(CH$_2$)$_m$C(=O)Het, —S(CH$_2$)$_m$C(=O)NR$^a$R$^a$, —S(CH$_2$)$_m$C(=O)OR$^a$, —S(CH$_2$)$_m$NR$^a$R$^a$, —S(CH$_2$)$_m$OR$^a$, —R$^b$OR$^a$, —SR$^a$, —C(=O)NR$^a$R$^a$, —C(=O)NR$^a$OR$^a$, —C(=O)NR$^a$R$^b$NR$^a$R$^a$, —C(=O)NR$^a$R$^b$OR$^a$, —C(=O)NR$^a$R$^b$S(=O)$_n$R$^a$, —C(=O)NR$^a$R$^b$Het, —C(=O)OR$^a$, —OC(=O)R$^a$, —C(=O)OR$^b$NR$^a$R$^a$, —C(=O)R$^a$, —C(=O)R$^b$NR$^a$R$^a$, —C(=NOR$^a$)R$^a$, —C(=NCN)R$^a$, —S(=O)$_2$NR$^a$R$^a$, —NR$^a$S(=O)$_2$R$^a$, —S(=O)$_2$NR$^a$R$^b$C(=O)NR$^a$R$^a$, or —S(=O)$_2$NR$^a$R$^b$C(=O)OR$^a$;

R$^a$ is, independently at each instance, H, C$_{1-6}$alkyl, —C(=O)C$_{1-6}$alkyl, C$_{1-4}$haloalkyl, phenyl, benzyl, or 5 or 6-memebered ring, saturated or unsaturated heterocycle containing 1,2,3, or 4 heteroatoms independently selected from N, O or S;

R$^b$ is, independently at each instance, C$_{1-6}$alkyl, —C(=O)C$_{1-4}$alkyl, C$_{1-4}$haloalkyl, phenyl, benzyl, or 5 or 6-memebered ring, saturated or unsaturated heterocycle containing 1,2,3, or 4 heteroatoms independently selected from N, O or S;

R$^c$ is C$_{1-6}$alkyl, C$_{1-4}$haloalkyl, phenyl or benzyl;

R$^d$ is phenyl substituted by 0, 1 or 2 groups selected from —CN, halogen, nitro, C$_{1-6}$alkyl, C$_{1-4}$haloalkyl, —OH, —OR$^c$, —NR$^a$R$^a$, —S(=O)$_n$R$^c$, —C(=O)NR$^a$R$^a$, —C(=O)OR$^a$, —NR$^a$C(=O)R$^a$, —OC(=O)R$^a$, B(OH)$_2$, vicinyl —OCH$_2$CH$_2$O—, vicinyl —OC$_{1-2}$haloalkylO—, vicinyl —OCH$_2$O—, vicinyl —CH$_2$OCH$_2$O—, phenyl, benzyl and a 5- or 6-membered ring, saturated or unsaturated heterocycle containing 1, 2, 3 or 4 heteroatoms independently selected from N, O, or S;

m is 1, 2 or 3;

n is 0, 1 or 2;

or a pharmaceutically acceptable salt thereof.

2. A compound as recited in claim 1 wherein:

A is N or CR$^{20}$ wherein R$^{20}$ is H, halogen, cyano, C$_{1-6}$alkyl, C$_{1-6}$alkenyl, C$_{1-6}$alkynyl, —OC$_{0-4}$alkyl, —N(C$_{0-4}$alkyl)(C$_{0-4}$alkyl).

3. A compound as recited in claim 1 wherein:

R$^I$ is H, halogen, cyano, nitro, C$_{1-6}$alkyl, C$_{1-6}$alkenyl, C$_{1-6}$alkynyl, S(=O)$_n$C$_{1-4}$alkyl, —S(=O)$_n$N(C$_{1-4}$alkyl)$_n$, —OC$_{0-4}$alkyl, —N(C$_{0-4}$alkyl)(C$_{0-4}$alkyl), —C(=O)OC$_{1-4}$alkyl, —C(=O) C$_{0-4}$alkyl, or —C(=O)N(C$_{0-4}$alkyl)(C$_{0-4}$alkyl) where n is 0, 1 or 2.

4. A compound as recited in claim 1 wherein:

R$^{II}$ is H, halogen, cyano, nitro, C$_{1-6}$alkyl, C$_{1-6}$alkenyl, C$_{1-6}$alkynyl, S(=O)$_n$C$_{1-4}$alkyl, —S(=O)$_n$N(C$_{1-4}$alkyl)$_n$, —OC$_{0-4}$alkyl, —N(C$_{0-4}$alkyl)(C$_{0-4}$alkyl), —C(=O)OC$_{1-4}$alkyl, —C(=O) C$_{0-4}$alkyl, or —C(=O)N(C$_{0-4}$alkyl)(C$_{0-4}$alkyl) where n is 0, 1 or 2.

5. A compound as recited in claim 1 wherein:

R$^3$ is selected from formulas (i), (ii), (iii) or (iv) set forth below:

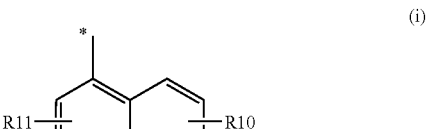

(i)

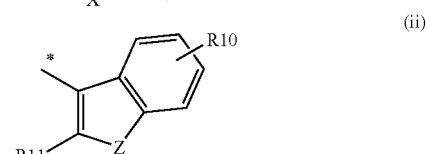

(ii)

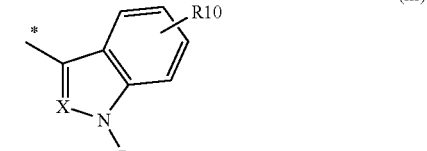

(iii)

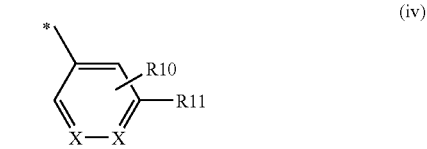

(iv)

wherein * is the location where (i) or (ii) or (iii) or (iv) is attached to structural formula (I), and X is C or N; and Z is O or S, wherein $R^{10}$ is at any position on the ring and $R^{10}$ and $R^{11}$ are independently at each instance H, $R^a$, halogen, —CN, nitro, $OR^a$, $CF_3$, —$NR^aR^a$, —$C(=O)OR^a$, —$C(=O)R^a$, —$C(=O)NR^aR^a$, —$OC(=O)C_{1-4}alkyl$, —$NR^aC(=O)C_{1-4}alkyl$ or —$S(=O)_nR^c$; and wherein $R^{11a}$ is $R^a$, —$S(=O)_2NR^aR^a$ or —$S(=O)_nR^c$ and n=1 or 2.

6. A compound as recited in claim 1 wherein:

$R^4$ is selected from formulas (a) to (z) or (aa) or (ab) set forth below:

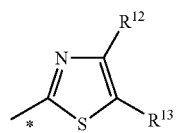 (a)

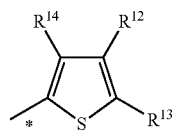 (b)

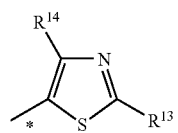 (c)

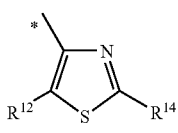 (d)

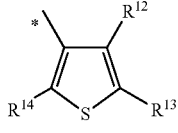 (e)

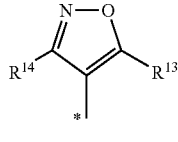 (f)

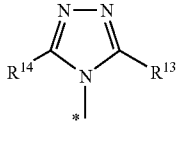 (g)

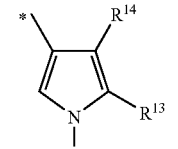 (h)

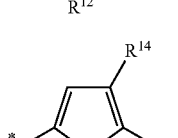 (i)

-continued

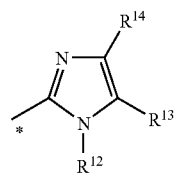 (j)

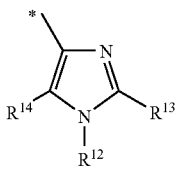 (k)

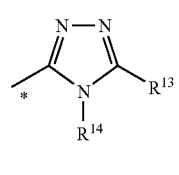 (l)

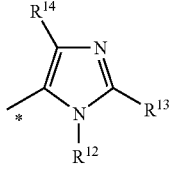 (m)

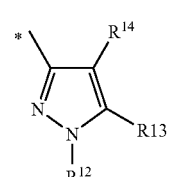 (n)

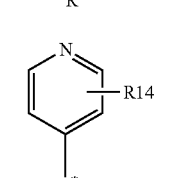 (o)

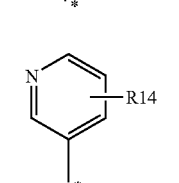 (p)

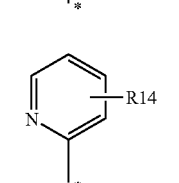 (q)

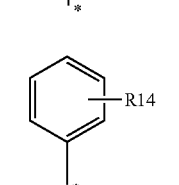 (r)

-continued (s) 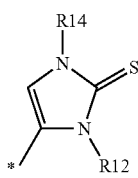

(t) 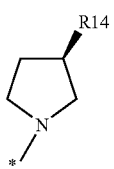

(u) 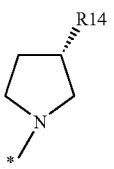

(v) 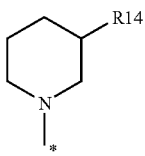

(w) 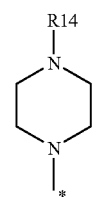

(x) 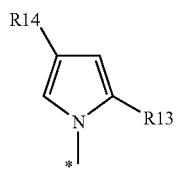

(y) 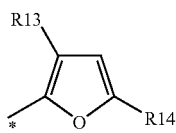

(z) 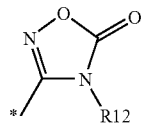

(aa) 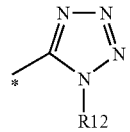

-continued (ab) 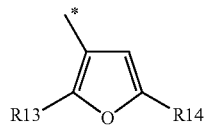

wherein * is the location wherein $R^4$ is attached to the ring system and wherein wherein $R^{12}$, $R^{13}$ and $R^{14}$ are each independently represented by H, Het, $C_{1-6}$alkyl, —CN, —NR$^a$R$^a$, -nitro, —C(=O)R$^a$, —C(=O)NR$^a$R$^a$, —C(=O)NR$^a$S(=O)$_2$R$^a$, —C(=O)NR$^a$-Het, —C(=O)NR$^a$NR$^a$R$^a$, —C(=O)NR$^a$(R$^b$NR$^a$R$^a$), —C(=O)NR$^a$(R$^b$OR$^a$), —C(=O)NR$^a$(R$^b$S(=O)$_2$R$^a$), —C(=O)NR$^a$R$^b$Het, —C(=O)NR$^a$OR$^a$, —C(=O)R$^b$NR$^a$R$^a$, —C(=NOR$^a$)R$^a$, —C(=NCN)R$^a$, —C(=O)OR$^a$, —C(=O)OR$^b$NR$^a$R$^a$, —C(=O)R$^a$, —OC(=O)R$^a$, —C(=O)R$^a$—SR$^a$, =S, —NR$^a$C(=O)R$^a$, —NR$^a$C(=O)OR$^a$, —NR$^a$S(=O)$_2$R$^b$, —C(=NOR$^a$)R$^a$, —S(=O)$_2$R$^a$, —S(=O)$_2$NR$^a$R$^a$, —S(=O)$_2$NR$^a$(R$^b$C(=O)NR$^a$R$^a$), or —S(=O)$_2$NR$^a$(R$^b$C(=O)OR$^a$.

7. A compound as recited in claim 1 wherein:

A is N or CR$^{20}$ wherein R$^{20}$ is H, halogen, cyano, $C_{1-6}$alkyl, $C_{1-6}$alkenyl, $C_{1-6}$alkynyl, —OC$_{0-4}$alkyl, —N(C$_{0-4}$alkyl)(C$_{0-4}$alkyl);

R$^I$ is H, halogen, cyano, nitro, $C_{1-6}$alkyl, $C_{1-6}$alkenyl, $C_{1-6}$alkynyl, S(=O)$_n$C$_{1-4}$alkyl, —S(=O)$_n$N(C$_{1-4}$alkyl)$_n$, —OC$_{0-4}$alkyl, —N(C$_{0-4}$alkyl)(C$_{0-4}$alkyl), —C(=O)OC$_{1-4}$alkyl, —C(=O) C$_{0-4}$alkyl, or —C(=O)N(C$_{0-4}$alkyl)(C$_{0-4}$alkyl) where n is 0, 1 or 2;

R$^{II}$ is H, halogen, cyano, nitro, $C_{1-6}$alkyl, $C_{1-6}$alkenyl, $C_{1-6}$alkynyl, S(=O)$_n$C$_{1-4}$alkyl, —S(=O)$_n$N(C$_{1-4}$alkyl)$_n$, —OC$_{0-4}$alkyl, —N(C$_{0-4}$alkyl)(C$_{0-4}$alkyl), —C(=O)OC$_{1-4}$alkyl, —C(=O) C$_{0-4}$alkyl, or —C(=O)N(C$_{0-4}$alkyl)(C$_{0-4}$alkyl) where n is 0, 1 or 2;

R$^2$ is —CH$_2$CH$_2$CH$_3$, —CH$_2$-cyclopropyl, —CH$_2$CH(CH$_3$)$_2$, —CH$_2$CH$_2$CH$_2$F, —CH$_2$-cyclobutyl, —CH$_2$C(CH$_3$)$_3$, —CH$_2$CH$_2$CH(CH$_3$)$_2$, —CH$_2$CF$_3$, —CH$_2$-methylphenyl, —CH$_2$-phenol, —CH$_2$-(3,5-dimethylisoxazol-4-yl), —CH$_2$—S-phenyl, —CH$_2$-phenylcarboxyl, or —CH$_2$SCF$_3$;

R$^3$ is selected from formulas (i), (ii), (iii) or (iv) set forth below:

(i) 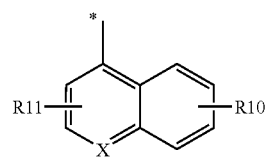

(ii) 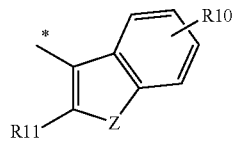

-continued

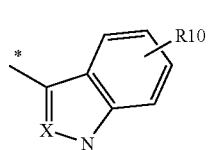
(iii)

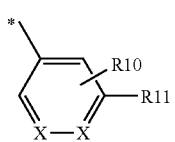
(iv)

wherein * is the location where (i) or (ii) or (iii) or (iv) is attached to structural formula (II), and X is C or N; and Z is O or S, wherein $R^{10}$ is at any position on the ring and $R^{10}$ and $R^{11}$ are independently at each instance H, $R^a$, halogen, —CN, nitro, $OR^a$, $CF_3$, —$NR^aR^a$, —C(=O)$OR^a$, —C(=O)$R^a$, —C(=O)$NR^aR^a$, —OC(=O)$C_{1-4}$alkyl, —$NR^aC$(=O)$C_{1-4}$alkyl or —S(=O)$_nR^c$; and wherein $R^{11a}$ is $R^a$, —S(=O)$_2NR^aR^a$ or —S(=O)$_nR^c$ and n=1 or 2;

$R^4$ is selected from formulas (a) to (z) or (aa) or (ab) set forth below:

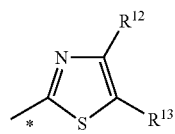
(a)

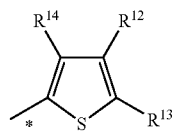
(b)

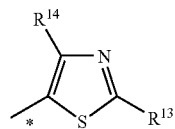
(c)

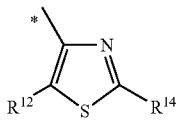
(d)

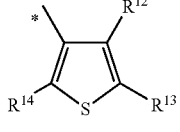
(e)

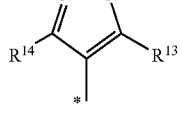
(f)

-continued

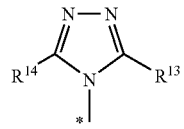
(g)

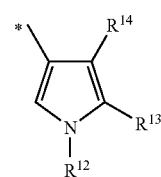
(h)

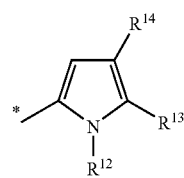
(i)

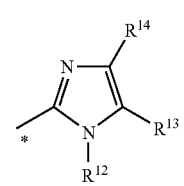
(j)

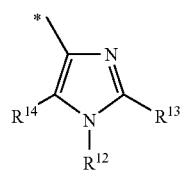
(k)

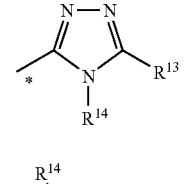
(l)

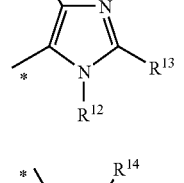
(m)

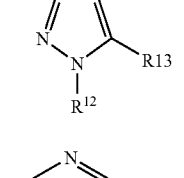
(n)

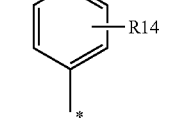
(o)

-continued (p) 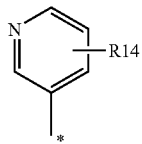

(q) 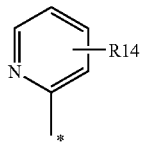

(r) 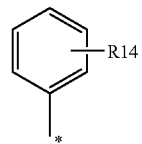

(s) 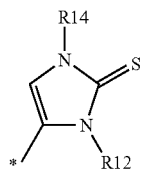

(t) 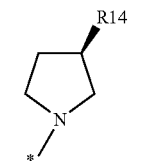

(u) 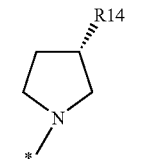

(v) 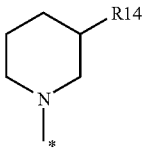

(w) 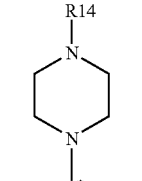

(x) 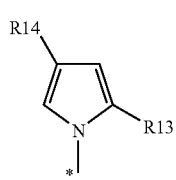

-continued (y) 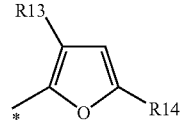

(z) 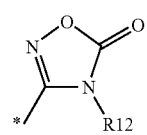

(aa) 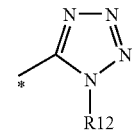

(ab) 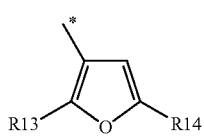

wherein * is the location wherein R⁴ is attached to the ring system and wherein wherein R¹², R¹³ and R¹⁴ are each independently represented by H, Het, C$_{1-6}$alkyl, —CN, —NR$^a$R$^a$, -nitro, —C(=O)R$^a$, —C(=O)NR$^a$R$^a$, —C(=O)NR$^a$S(=O)$_2$R$^a$, —C(=O)NR$^a$-Het, —C(=O)NR$^a$NR$^a$R$^a$, —C(=O)NR$^a$(R$^b$NR$^a$R$^a$), —C(=O)NR$^a$(R$^b$OR$^a$), —C(=O)NR$^a$(R$^b$S(=O)$_2$R$^a$), C(=O)NR$^a$R$^b$Het, —C(=O)NR$^a$OR$^a$, —C(=O)R$^b$NR$^a$R$^a$, —C(=NOR$^a$)R$^a$, —C(=NCN)R$^a$, —C(=O)OR$^a$, —C(=O)OR$^b$NR$^a$R$^a$, —C(=O)R$^a$, —OC(=O)R$^a$, —C(=O)R$^a$—SR$^a$, =S, —NR$^a$C(=O)R$^a$, —NR$^a$C(=O)OR$^a$, —NR$^a$S(=O)$_2$R$^b$, —C(=NOR$^a$)R$^a$, —S(=O)$_2$R$^a$, —S(=O)$_2$NR$^a$R$^a$, —S(=O)$_2$NR$^a$(R$^b$C(=O)NR$^a$R$^a$), or —S(=O)$_2$NR$^a$(R$^b$C(=O)OR$^a$.

8. A compound of claim 1 selected from:

5-[8-[(6-chloroquinolin-4-yl)methyl]-6-(cyclopropylmethyl)-5-oxo-6,8-dihydro-5H-pyrazolo[4,3-e][1,2,4]triazolo[4,3-c]pyrimidin-9-yl]-1-methyl-1H-pyrrole-3-carbonitrile;

5-[8-[(6-chloroquinolin-4-yl)methyl]-6-(cyclopropylmethyl)-3-methyl-5-oxo-6,8-dihydro-5H-pyrazolo[4,3-e][1,2,4]triazolo[4,3-c]pyrimidin-9-yl]-1-methyl-1H-pyrrole-3-carbonitrile;

5-[8-[(6-chloroquinolin-4-yl)methyl]-6-(cyclopropylmethyl)-3-(dimethylamino)-5-oxo-6,8-dihydro-5H-pyrazolo[4,3-e][1,2,4]triazolo[4,3-c]pyrimidin-9-yl]-1-methyl-1H-pyrrole-carbonitrile;

5-[3-amino-8-[(6-chloroquinolin-4-yl)methyl]-6-(cyclopropylmethyl)-5-oxo-6,8-dihydro-5H-pyrazolo[4,3-e][1,2,4]triazolo[4,3-c]pyrimidin-9-yl]-1-methyl-1H-pyrrole-3-carbonitrile;

5-[8-[(6-chloroquinolin-4-yl)methyl]-6-(cyclopropylmethyl)-5-oxo-6,8-dihydro-5H-imidazo[1,2-c]pyrazolo[4,3-e]pyrimidin-9-yl]-1-methyl-1H-pyrrole-3-carbonitrile;

5-[8-[(6-chloroquinolin-4-yl)methyl]-6-(cyclopropylmethyl)-3-methyl-5-oxo-6,8-dihydro-5H-imidazo[1,2-c]pyrazolo[4,3-e]pyrimidin-9-yl]-1-methyl-1H-pyrrole-3-carbonitrile;

8-[(6-chloroquinolin-4-yl)methyl]-6-(cyclopropylm-ethyl)-9-(1-methyl-1H-imidazol-5-yl)-6,8-dihydro-5H-imidazo[1,2-c]pyrazolo[4,3-e]pyrimidin-5-one;

8-{[5-chloro-1-(methylsulfonyl)-1H-indol-3-yl]methyl}-6-(cyclopropylmethyl)-9-(1-methyl-1H-imidazol-5-yl)-6,8-dihydro-5H-imidazo[1,2-c]pyrazolo[4,3-e]pyrimidin-5-one;

8-[(6-chloroquinolin-4-yl)methyl]-6-(cyclopropylm-ethyl)-9-[1-methyl-4-(methylsulfonyl)-1H-pyrrol-2-yl]-6,8-dihydro-5H-imidazo[1,2-c]pyrazolo[4,3-e]pyrimidin-5-one;

5-[8-{[5-chloro-1-(methylsulfonyl)-1H-indol-3-yl]methyl}-6-(cyclopropylmethyl)-5-oxo-6,8-dihydro-5H-imidazo[1,2-c]pyrazolo[4,3-e]pyrimidin-9-yl]-1-methyl- 1H-pyrrole-3-carbonitrile.

9. A compound having the structural formula (II):

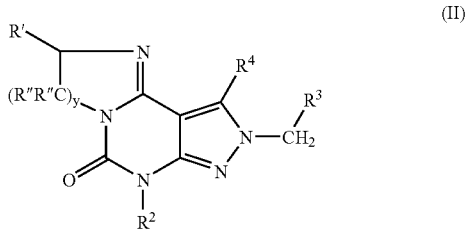

(II)

wherein,

R' is H, alkyl, alkenyl, alkynyl;

R" is independently at each instance H, alkyl, alkenyl, alkynyl;

y is 1 or 2;

$R^2$ is H, alkyl, wherein said alkyl is optionally substituted with 0, 1, 2 or 3 substituents selected from heterocycle, $S(=O)_nR^c$, $-S(=O)_nNR^aR^a$ halogen, —CN, —$OR^a$, —$NR^aR^a$, —$C(=O)OR^a$, —$C(=O)R^a$, —$C(=O)NR^aR^a$, —$OC(=O)C_{1-4}$alkyl, or —$NR^aC(=O)C_{1-4}$alkyl, alkylcycloalkyl, wherein said alkylcycloalkyl is optionally substituted with 0, 1, 2 or 3 substituents selected from heterocycle, $S(=O)_nR^c$, —$S(=O)_nNR^aR^a$ halogen, —CN, —$OR^a$, —$NR^aR^a$, —$C(=O)OR^a$, —$C(=O)R^a$, —$C(=O)NR^aR^a$, —$OC(=O)C_{1-4}$alkyl, or —$NR^aC(=O)C_{1-4}$alkyl, alkenyl, alkynyl, cycloalkyl, cycloalkenyl, cycloalkynyl, aryl, alkoxy, amino, or heterocycle;

$R^3$ is a monocyclic or bicyclic, saturated or unsaturated, ring system comprising 0, 1, 2 or 3 heteroatoms independently selected from N, O, or S, the ring being substituted by 0, 1, 2 or 3 substituents selected from =O, halogen, —$OR^a$, $C_{1-6}$alkyl, $C_{1-6}$haloalkyl, —CN, nitro, —$S(=O)_nR^c$, —$O(CH_2)_m$Het, —$O(CH_2)_mC(=O)$Het, —$O(CH_2)_mC(=O)NR^aR^a$, —$O(CH_2)_mC(=O)OR^a$, —$O(CH_2)_mNR^aR^a$, —$O(CH_2)_mOR^a$, —$S(CH_2)_m$Het, —$S(CH_2)_mC(=O)$Het, —$S(CH_2)_mC(=O)NR^aR^a$, —$S(CH_2)_mC(=O)OR^a$, $S(CH_2)_mNR^aR^a$, —$S(CH_2)_mOR^a$, —$NR^aR^a$, —$NHC(=O)R^a$, N=$NR^a$, aminocarbonyl, phenyl, benzyl; or $R^3$ is represented by -Het, -Het-Het, $R^5$,—$R^5$-Het, -Het-$R^5$, -Het-O—$R^5$, —$R^5$—$R^5$, —$R^5$—$OR^5$;

$R^4$ is a monocyclic or bicyclic, saturated or unsaturated, ring system, or a vicinal-fused derivative thereof, which may contain from 5 to 12 ring atoms, 0, 1, 2, 3 or 4 of which are heteroatoms independently selected from N, O, or S, the ring system being substituted by 0, 1, 2 or 3 substituents selected from $B(OH)_2$, vicinal —$OCH_2CH_2O$—, vicinal —$OC_{1-2}$haloalkylO—, vicinal —$OCH_2O$—, vicinal —$CH_2OCH_2O$—, =O, halogen, —$R^bOR^a$, —$SR^a$, —$OR^a$, $C_{1-6}$alkyl, $C_{1-6}$haloalkyl, —CN, —$S(=O)_nR^c$, —$O(CH_2)_m$Het, —$O(CH_2)_mC(=O)$Het, —$O(CH_2)_mC(=O)NR^aR^a$, —$O(CH_2)_mC(=O)OR^a$, —$O(CH_2)_mNR^aR^a$, —$O(CH_2)_mOR^a$, —$S(CH_2)_m$Het, —$S(CH_2)_mC(=O)$Het, —$S(CH_2)_mC(=O)NR^aR^a$, —$S(CH_2)_mC(=O)OR^a$, —$S(CH_2)_mNR^aR^a$, —$S(CH_2)_mOR^a$, —$NR^aR^a$, —$NHC(=O)R^a$, —$NHC(=O)OR^a$, N=$NR^a$, $NO_2$, —$C(=O)NR^aR^a$, —$C(=O)NR^aOR^a$, —$C(=O)NR^a(R^bNR^aR^a)$, —$C(=O)NR^a(R^bOR^a)$, —$C(=O)NR^a(R^bS(=O)_nR^a)$, $C(=O)NR^a(R^b$Het), —$C(=O)OR^a$, —$OC(=O)R^a$, —$C(=O)OR^bNR^aR^a$, —$C(=O)R^a$, $C(=O)R^bNR^aR^a$, —$C(=NOR^a)R^a$, —$C(=NCN)R^a$, —$S(=O)_2NR^aR^a$, —$NR^aS(=O)_2R^a$, —$S(=O)_2NR^a(R^bC(=O)NR^aR^a)$, —$S(=O)_2NR^a(R^bC(=O)OR^a)$, aminocarbonyl, phenyl, benzyl; or $R^4$ is represented by —$(CH_2)_nR^5$-Het, —$(CH_2)_nR^d$, -Het, -Het-Het, $R^5$, —$R^5$-Het, -Het-$R^5$, -Het-$OR^5$, $R^5$—$R^5$, or —$R^5$—$OR^5$; or $R^4$ is represented by $C_{1-6}$alkyl, —$NC_{1-6}$alkyl, or —$N(C_{1-6}$alkyl$)_2$ wherein the $C_{1-6}$alkyl, —$NC_{1-6}$alkyl, —$N(C_{1-6}$alkyl) are substituted by 0, 1 or 2 substituents selected from $R^a$, $OR^a$, halogen or phenyl wherein $R^4$ is not —$(CH_2)_zCH_3$, —$(CH_2)_zCH_2OH$, —$(CH_2)_zCO_2H$, or —$(CH_2)_zCO_2C_{1-6}$alkyl wherein z is 1,2,3,4, 5, or 6;

$R^5$ is independently at each instance, phenyl substituted by 0, 1, 2, or 3 groups selected from halogen, $C_{1-6}$haloalkyl, —$OC_{1-6}$haloalkyl, $C_{1-6}$alkyl, —CN, nitro, —$OR^a$, —$S(=O)_nR^c$, —$O(CH_2)_m$Het, —$O(CH_2)_mC(=O)$Het, —$O(CH_2)_mC(=O)NR^aR^a$, —$O(CH_2)_mC(=O)OR^a$, —$O(CH_2)_mNR^aR^a$, —$O(CH_2)_mOR^a$, —$S(CH_2)_m$Het, —$S(CH_2)_mC(=O)$Het, —$S(CH_2)_mC(=O)NR^aR^a$, —$S(CH_2)_mC(=O)OR^a$, —$S(CH_2)_mN$-$R^aR^a$, —$S(CH_2)_mOR^a$, —$R^bOR^a$, —$SR^a$, —$C(=O)NR^aR^a$, —$C(=O)NR^aOR^a$, —$C(=O)NR^aR^bNR^aR^a$, —$C(=O)NR^aR^bOR^a$, —$C(=O)NR^aR^bS(=O)_nR^a$, —$C(=O)NR^aR^b$Het, —$C(=O)OR^a$, —$OC(=O)R^a$, —$C(=O)OR^bNR^aR^a$, —$C(=O)R^a$, —$C(=O)R^bN$-$R^aR^a$, —$C(=NOR^a)R^a$, —$C(=NCN)R^a$, —$S(=O)_2NR^aR^a$, —$NR^aS(=O)_2R^a$, —$S(=O)_2NR^aR^bC(=O)NR^aR^a$, or —$S(=O)_2NR^aR^bC(=O)OR^a$;

$R^a$ is, independently at each instance, H, $C_{1-6}$alkyl, —$C(=O)C_{1-4}$alkyl, $C_{1-4}$haloalkyl, phenyl, benzyl, or 5 or 6-memebered ring, saturated or unsaturated heterocycle containing 1,2,3, or 4 heteroatoms independently selected from N, O or S;

$R^b$ is, independently at each instance, $C_{1-6}$alkyl, —$C(=O)C_{1-4}$alkyl, $C_{1-4}$haloalkyl, phenyl, benzyl, or 5 or 6-memebered ring, saturated or unsaturated heterocycle containing 1,2,3, or 4 heteroatoms independently selected from N, O or S;

$R^c$ is $C_{1-6}$alkyl, $C_{1-4}$haloalkyl, phenyl or benzyl;

$R^d$ is phenyl substituted by 0, 1 or 2 groups selected from —CN, halogen, nitro, $C_{1-6}$alkyl, $C_{1-4}$haloalkyl, —OH, —$OR^c$, —$NR^aR^a$, —$S(=O)_nR^c$, —$C(=O)NR^aR^a$, —$C(=O)OR^a$, —$NR^aC(=O)R^a$, —$OC(=O)R^a$, $B(OH)_2$, vicinyl —$OCH_2CH_2O$—, vicinyl —$OC_{1-2}$haloalkylO—, vicinyl —$OCH_2O$—, vicinyl —$CH_2OCH_2O$—, phenyl, benzyl and a 5- or 6-membered ring, saturated or unsaturated heterocycle containing 1, 2, 3 or 4 heteroatoms independently selected from N, O, or S;

m is 1, 2 or 3;

n is 0, 1 or 2;

or a pharmaceutically acceptable salt thereof.

10. A compound as recited in claim 9 wherein:

R' is H, $C_{1-6}$alkyl, $C_{1-6}$alkenyl, $C_{1-6}$alkynyl.

11. A compound as recited in claim 9 wherein:

R" is independently at each instance H, $C_{1-6}$alkyl, $C_{1-6}$alkenyl, $C_{1-6}$alkynyl.

12. A compound as recited in claim 9 wherein:

$R^3$ is selected from formulas (i), (ii), (iii) or (iv) set forth below:

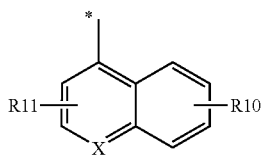

(i)

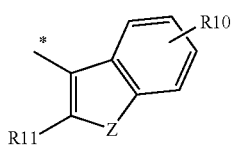

(ii)

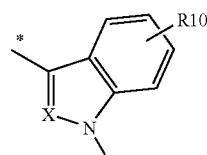

(iii)

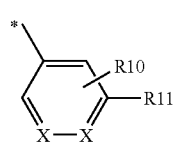

(iv)

wherein * is the location where (i) or (ii) or (iii) or (iv) is attached to structural formula (I), and X is C or N; and Z is O or S, wherein $R^{10}$ is at any position on the ring and $R^{10}$ and $R^{11}$ are independently at each instance H, $R^a$, halogen, —CN, nitro, $OR^a$, $CF_3$, —$NR^aR^a$, —C(=O)$OR^a$, —C(=O)$R^a$, —C(=O)$NR^aR^a$, —OC(=O)$C_{1-4}$alkyl, —$NR^aC(=O)C_{1-4}$alkyl or —S(=O)$_nR^c$; and wherein $R^{11a}$ is $R^a$, —S(=O)$_2NR^aR^a$ or —S(=O)$_nR^c$ and n=1 or 2.

13. A compound as recited in claim 9 wherein:

$R^4$ is selected from formulas (a) to (z) or (aa) or (ab) set forth below:

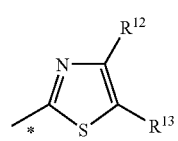

(a)

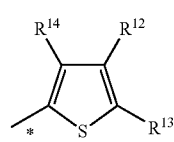

(b)

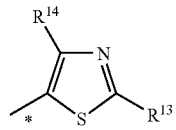

(c)

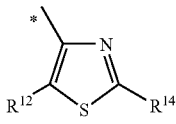

(d)

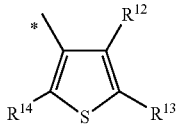

(e)

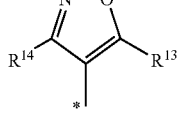

(f)

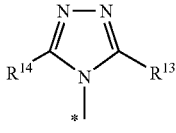

(g)

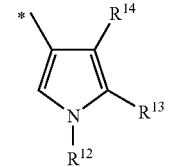

(h)

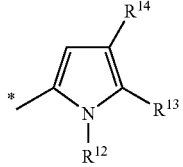

(i)

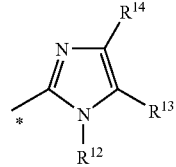

(j)

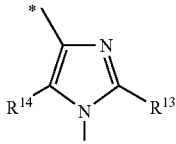

(k)

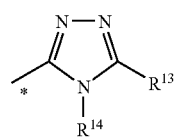

(l)

-continued

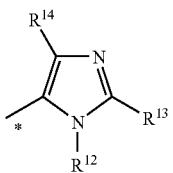 (m)

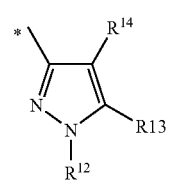 (n)

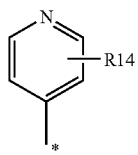 (o)

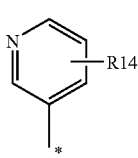 (p)

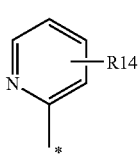 (q)

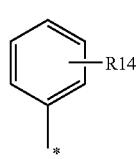 (r)

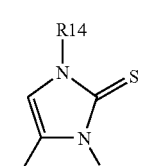 (s)

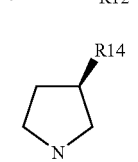 (t)

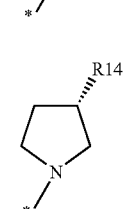 (u)

-continued

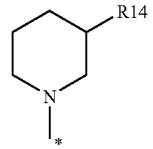 (v)

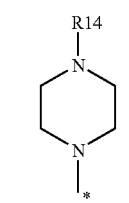 (w)

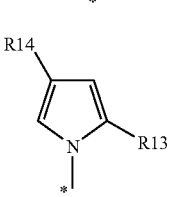 (x)

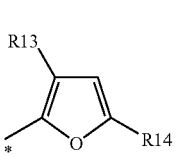 (y)

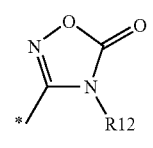 (z)

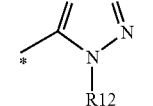 (aa)

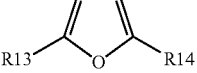 (ab)

wherein * is the location wherein $R^4$ is attached to the ring system and wherein wherein $R^{12}$, $R^{13}$ and $R^{14}$ are each independently represented by H, Het, $C_{1-6}$alkyl, —CN, —$NR^aR^a$, -nitro, —C(=O)$R^a$, —C(=O)$NR^aR^a$, —C(=O)$NR^aS(=O)_2R^a$, —C(=O)$NR^a$-Het, —C(=O)$NR^aNR^aR^a$, —C(=O)$NR^a(R^bNR^aR^a)$, —C(=O)$NR^a(R^bOR^a)$, —C(=O)$NR^a(R^bS(=O)_2R^a)$, —C(=O)$NR^aR^b$Het, —C(=O)$NR^aOR^a$, —C(=O)$R^bNR^aR^a$, —C(=$NOR^a$)$R^a$, —C(=NCN)$R^a$, —C(=O)$OR^a$, —C(=O)$OR^bNR^aR^a$, —C(=O)$R^a$, —OC(=O)$R^a$, —C(=O)$R^aSR^a$, =S, —$NR^aC(=O)R^a$, —$NR^aC(=O)OR^a$, —$NR^aS(=O)_2R^b$, —C(=$NOR^a$)$R^a$, —S(=O)$_2R^a$, —S(=O)$_2NR^aR^a$, —S(=O)$_2NR^a(R^bC(=O)NR^aR^a)$, or —S(=O)$_2NR^a(R^bC(=O)OR^a$.

14. A compound as recited in claim 9 wherein:
R' is H, $C_{1-6}$alkyl, $C_{1-6}$alkenyl, $C_{1-6}$alkynyl;
R" is independently at each instance H, $C_{1-6}$alkyl, $C_{1-6}$alkenyl, $C_{1-6}$alkynyl;
y is 1;

R² is —(CH₂CH₂CH₃, —CH₂-cyclopropyl, —CH₂CH(CH₃)₂, —(CH₂CH₂CH₂F, —CH₂-cyclobutyl, —CH₂C(CH₃)₃, —(CH₂CH₂CH(CH₃)₂, —CH₂CF₃, —CH₂-methylphenyl, —(CH₂-phenol, —CH₂-(3,5-dimethylisoxazol-4-yl), —CH₂—S-phenyl, —CH₂-phenylcarboxyl, or —CH₂SCF₃;

R³ is selected from formulas (i), (ii), (iii) or (iv) set forth below:

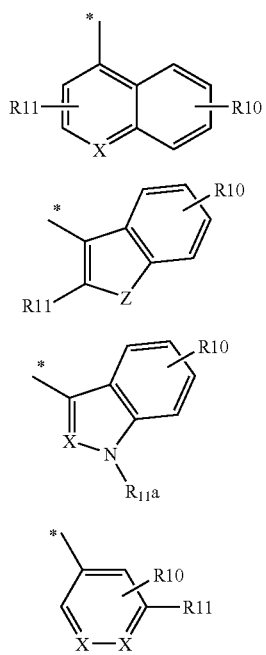

wherein * is the location where (i) or (ii) or (iii) or (iv) is attached to structural formula (I), and X is C or N; and Z is O or S, wherein R¹⁰ is at any position on the ring and R¹⁰ and R¹¹ are independently at each instance H, Rᵃ, halogen, —CN, nitro, ORᵃ, CF₃, —NRᵃRᵃ, C(=O)ORᵃ, —C(=O)Rᵃ, —C(=O)NRᵃRᵃ, —OC(=O)C₁₋₄alkyl, —NRᵃC(=O)C₁₋₄alkyl or —S(=O)ₙRᶜ; and wherein R¹¹ᵃ is Rᵃ, —S(=O)₂NRᵃRᵃ or —S(=O)ₙRᶜ and n=1 or 2;

R⁴ is selected from formulas (a) to (z) or (aa) or (ab) set forth below:

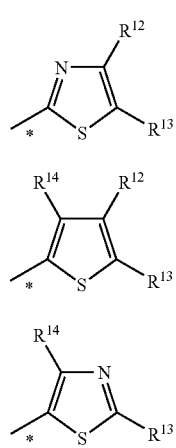

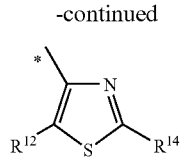 (d)

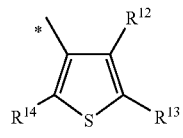 (e)

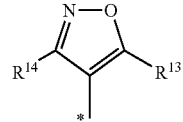 (f)

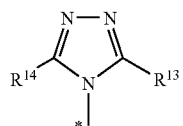 (g)

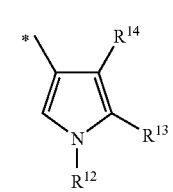 (h)

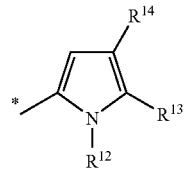 (i)

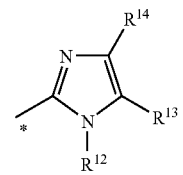 (j)

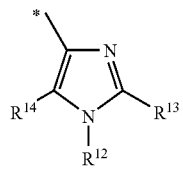 (k)

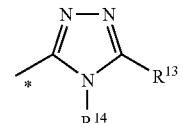 (l)

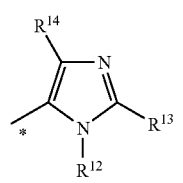 (m)

-continued (n) 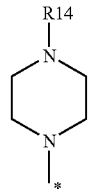  (w)

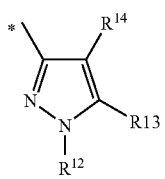

(o) 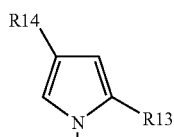  (x)

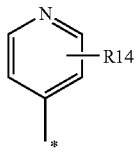

(p) 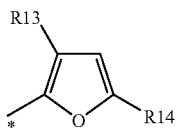  (y)

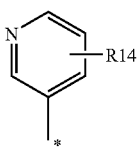

(q) 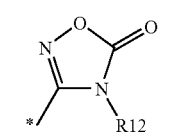  (z)

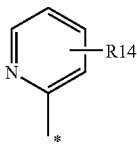

(r) 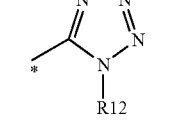  (aa)

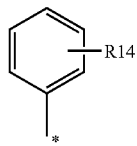

(s) 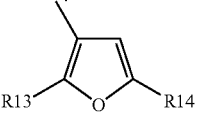  (ab)

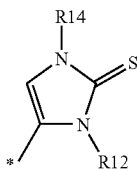

wherein * is the location wherein $R^4$ is attached to the ring system and wherein wherein $R^{12}$, $R^{13}$ and $R^{14}$ are each independently represented by H, Het, $C_{1-6}$alkyl, —CN, —NR$^a$R$^a$, -nitro, —C(=O)R$^a$, —C(=O)NR$^a$R$^a$, —C(=O)NR$^a$S(=O)$_2$R$^a$, —C(=O)NR$^a$-Het, —C(=O)NR$^a$NR$^a$R$^a$, —C(=O)NR$^a$(R$^b$NR$^a$R$^a$), —C(=O)NR$^a$(R$^b$OR$^a$), —C(=O)NR$^a$(R$^b$S(=O)$_2$R$^a$), —C(=O)NR$^a$R$^b$Het, —C(=O)NR$^a$OR$^a$, —C(=O)R$^b$NR$^a$R$^a$, —C(=NOR$^a$)R$^a$, —C(=NCN)R$^a$, —C(=O)OR$^a$, —C(=O)OR$^b$NR$^a$R$^a$, —C(=O)R$^a$, —OC(=O)R$^a$, —C(=O)R$^a$—SR$^a$, =S, —NR$^a$C(=O)R$^a$, —NR$^a$C(=O)OR$^a$, —NR$^a$S(=O)$_2$R$^b$, —C(=NOR$^a$)R$^a$, —S(=O)$_2$R$^a$, S(=O)$_2$NR$^a$R$^a$, S(=O)$_2$NR$^a$(R$^b$C(=O)NR$^a$R$^a$), or —S(=O)$_2$NR$^a$(R$^b$C(=O)OR$^a$.

(t) 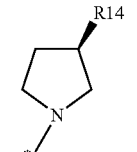

15. A compound of claim 1 selected from:

5-{8-[(6-chloroquinolin-4-yl)methyl]-6-isobutyl-5-oxo-2,5,6,8-tetrahydro-3H-imidazo[1,2-c]pyrazolo[4,3-e]pyrimidin-9-yl}-1-methyl-1H-pyrrole-3-carbonitrile;5-{8-[(6-chloroquinolin-4-yl)methyl]-6-isobutyl-5-oxo-2,5,6,8-tetrahydro-3H-imidazo[1,2-c]pyrazolo[4,3-e]pyrimidin-9-yl}-1-methyl-1H-pyrrole-3-carbonitrile;

(u) 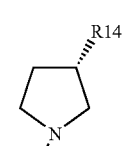

5-[8-[(6-chloroquinolin-4-yl)methyl]-6-(cyclopropylmethyl)-3-methyl-5-oxo-2,5,6,8-tetrahydro-3H-imidazo[1,2-c]pyrazolo[4,3-e]pyrimidin-9-yl]-1-methyl-1H-pyrrole-3-carbonitrile;

(v) 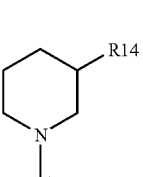

5-[8-[(6-chloroquinolin-4-yl)methyl]-6-(cyclopropylmethyl)-2-methyl-5-oxo-2,5,6,8-tetrahydro-3H-imidazo[1,2-c]pyrazolo[4,3-e]pyrimidin-9-yl]-1-methyl-1H-pyrrole-3-carbonitrile;

5-[(3R)-8-[(6-chloroquinolin-4-yl)methyl]-6-(cyclopropylmethyl)-3-methyl-5-oxo-2,5,6,8-tetrahydro-3H-imidazo[1,2-c]pyrazolo[4,3-e]pyrimidin-9-yl]-1-methyl-1H-pyrrole-3-carbonitrile;

5-[(3 S)-8-[(6-chloroquinolin-4-yl)methyl]-6-(cyclopropylmethyl)-3-methyl-5-oxo-2,5,6,8-tetrahydro-3H-imidazo[1,2-c]pyrazolo[4,3-e]pyrimidin-9-yl]-1-methyl-1H-pyrrole-3-carbonitrile;

5-[9-[(6-chloroquinolin-4-yl)methyl]-7-(cyclopropylmethyl)-6-oxo-2,3,4,6,7,9-hexahydropyrazolo[4,3-e]pyrimido[1,2-c]pyrimidin-10-yl]-1-methyl-1H-pyrrole-3-carbonitrile.

16. A method for the treatment of infection with *H. pylori* comprising administering to a host in need of such treatment a therapeutically effective amount of a compound as defined in claim 1.

17. A pharmaceutical composition comprising a compound as defined in claim 1 together with at least one pharmaceutically acceptable carrier, diluent or excipent.

* * * * *